United States Patent
Liu et al.

(10) Patent No.: US 10,696,728 B2
(45) Date of Patent: Jun. 30, 2020

(54) POLYPEPTIDES, RELATED NUCLEIC ACIDS, AND THEIR USES FOR CELL MODULATION AND TREATMENTS

(71) Applicants: Chunlei Liu, Orinda, CA (US); Eric Benner, Durham, NC (US)

(72) Inventors: Chunlei Liu, Orinda, CA (US); Eric Benner, Durham, NC (US)

( * ) Notice: Subject to any disclaimer, the term of this patent is extended or adjusted under 35 U.S.C. 154(b) by 0 days.

(21) Appl. No.: 15/320,349

(22) PCT Filed: Jul. 2, 2015

(86) PCT No.: PCT/US2015/038948
§ 371 (c)(1),
(2) Date: Dec. 20, 2016

(87) PCT Pub. No.: WO2016/004281
PCT Pub. Date: Jan. 7, 2016

(65) Prior Publication Data
US 2017/0226179 A1 Aug. 10, 2017

Related U.S. Application Data

(60) Provisional application No. 62/020,470, filed on Jul. 3, 2014.

(51) Int. Cl.
*C07K 14/705* (2006.01)
*A61K 38/00* (2006.01)
*A61N 2/00* (2006.01)
*C07K 14/81* (2006.01)
*A61N 2/02* (2006.01)
*A61K 41/00* (2020.01)

(52) U.S. Cl.
CPC ........ *C07K 14/705* (2013.01); *A61K 41/0057* (2013.01); *A61N 2/002* (2013.01); *A61N 2/008* (2013.01); *A61N 2/02* (2013.01); *C07K 14/8139* (2013.01); *A61K 38/00* (2013.01); *C07K 2319/00* (2013.01)

(58) Field of Classification Search
CPC ... C07K 14/705; C07K 2319/00; A61K 38/00
See application file for complete search history.

(56) References Cited

U.S. PATENT DOCUMENTS

| 4,554,101 A | 11/1985 | Hopp |
| 2011/0034753 A1 | 2/2011 | Dobson et al. |
| 2014/0348825 A1 | 11/2014 | Friedman et al. |

FOREIGN PATENT DOCUMENTS

| WO | 2002/014369 A3 | 2/2002 |
| WO | 2005/087807 A1 | 9/2005 |
| WO | 2013/029025 A1 | 2/2013 |

OTHER PUBLICATIONS

International Search Report and Written Opinion from PCT/US2015/038948 dated Oct. 16, 2015, 15 pages.

Argyridis et al., "Quantitative magnetic susceptibility of the developing mouse brain reveals microstructural changes in the white matter." Neuroimage (2014) vol. 88, pp. 134-142.
Banghart et al., "Light-activated ion channels for remote control of neuronal firing." Nat Neurosci (2004) vol. 7, No. 12, pp. 1381-1386.
Caterina et al., "The capsaicin receptor: a heat-activated ion channel in the pain pathway" Nature (1997) vol. 389, pp. 816-824.
Chen et al., "Ultrasensitive fluorescent proteins for imaging neuronal activity." Nature (2013) vol. 499, pp. 295-300.
Chen et al., "Wireless magnetothermal deep brain stimulation." Science (2015) vol. 347, pp. 1477-1480.
Cho et al., "The calcium-activated chloride channel anoctamin 1 acts as a heat sensor in nociceptive neurons." Nature Neuroscience (2012) vol. 15, No. 7, pp. 1015-1021.
Chowdhury et al., "A molecular framework for temperature-dependent gating of ion channels." Cell (2014) vol. 158, No. 5, pp. 1148-1158.
Clapham et al., "A thermodynamic framework for understanding temperature sensing by transient receptor potential (TRP) channels." Proc Natl Acad Sci USA (2011) vol. 108, No. 49, pp. 19492-19497.
Coffman et al., "Regulatory effects of ferritin on angiogenesis" PNAS (2009) vol. 106, No. 2, pp. 570-575, plus supporting information (10 pages total).
Correll et al., "Cloning and pharmacological characterization of mouse TRPV1" Neuroscience Letters (2004) vol. 370, pp. 55-60.
Cozzi et al., "Overexpression of wild type and mutated human ferritin H-chain in HeLa cells: in vivo role of ferritin ferroxidase activity." The Journal of Biological Chemistry (2000) vol. 275, No. 33, pp. 25122-25129.
Creazzo et al., "Role of cardiac neural crest cells in cardiovascular development." Annu Rev Physiol (1998) vol. 60, pp. 267-286.
Deisseroth, "Optogenetics." Nat Methods (2011) vol. 8, No. 1, pp. 26-29.
Finazzi et al., "Biology of ferritin in mammals: an update on iron storage, oxidative damage and neurodegeneration." Archives of Toxicology (2014) vol. 88, No. 10, pp. 1787-1802.
Fosque et al., "Labeling of active neural circuits in vivo with designed calcium integrators." Science (2015) vol. 347, pp. 755-760.
Guler et al., "Heat-evoked activation of the ion channel, TRPV4." The Journal of Neuroscience (2002) vol. 22, No. 15, pp. 6408-6414.
Hentze et al., "Two to tango: regulation of Mammalian iron metabolism." Cell (2010) vol. 142, No. 1, pp. 24-38.

(Continued)

*Primary Examiner* — Ruixiang Li
(74) *Attorney, Agent, or Firm* — ALGM LLP; Harry J. Guttman

(57) ABSTRACT

Disclosed herein are inventive polypeptides (e.g., comprising a thermal sensitive ion channel or variant thereof and a domain 5 of kininogen 1 or variant or fragment thereof) and nucleic acid molecules encoding inventive polypeptides. Also disclosed are methods for modulating a cell comprising administering certain compositions (e.g., pharmaceutical compositions of the nucleic acid molecule) and applying a static magnetic field or an electromagnetic field. Methods for treating diseases or disorders in an animal (e.g., a human) comprising administering certain compositions (e.g., pharmaceutical compositions of the nucleic acid molecule) and applying a static magnetic field or an electromagnetic field, are further disclosed.

18 Claims, 18 Drawing Sheets
Specification includes a Sequence Listing.

(56) References Cited

OTHER PUBLICATIONS

Huang et al., "Remote control of ion channels and neurons through magnetic-field heating of nanoparticles" Nature Nanotechnology (2010) vol. 5, pp. 602-606.

Hutson et al., "Neural crest and cardiovascular development: a 20-year perspective." Birth Defects Research (Part C) (2003) vol. 69, No. 1, pp. 2-13.

Jayaraman et al., "Mechanism and cellular applications of a green fluorescent protein-based halide sensor." The Journal of Biological Chemistry (2000) vol. 275, No. 9, pp. 6047-6050.

Jin et al., "Single action potentials and subthreshold electrical events imaged in neurons with a fluorescent protein voltage probe." Neuron (2012) vol. 75, No. 5, pp. 779-785.

Kaur et al., "Chronic expression of H-ferritin in dopaminergic midbrain neurons results in an age-related expansion of the labile iron pool and subsequent neurodegeneration: implications for Parkinson's disease." Brain Research (2009) vol. 1297, pp. 17-22.

Kosmidis et al., "Ferritin overexpression in Drosophila glia leads to iron deposition in the optic lobes and late-onset behavioral defects." Neurobiology of Disease (2011) vol. 43, No. 1, pp. 213-219.

Kuhn et al., "Inducible gene targeting in mice." Science (1995) vol. 269, pp. 1427-1429.

Maingret et al., "TREK-1 is a heat-activated background K(+) channel." EMBO J (2000) vol. 19, No. 11, pp. 2483-2491.

Nagel et al., "Channelrhodopsin-2, a directly light-gated cation-selective membrane channel." Proc Natl Acad Sci USA (2003) vol. 100, No. 24, pp. 13940-13945.

Picard et al., "Role of ferritin in the control of the labile iron pool in murine erythroleukemia cells." The Journal of Biological Chemistry (1998) vol. 273, No. 25, pp. 15382-15386.

Neuroscience, 3rd edition. Edited by Purves et al. (2004) Sinauer Associates Press. Sunderland, Mass. USA (832 pages in four pdfs).

Neuroscience, 5th edition. Edited by Purves et al. (2011) Sinauer Associates Press. Sunderland, Mass. USA—Table of Contents only (12 pages).

Sauer "Inducible gene targeting in mice using the Cre/lox system." Methods (1998) vol. 14, No. 4, pp. 381-392.

Scheer et al., "Use of the Gal4-UAS technique for targeted gene expression in the zebrafish." Mechanisms of Development (1999) vol. 80, No. 2, pp. 153-158.

Stanley et al., "Radio-Wave Heating of Iron Oxide Nanoparticles Can Regulate Plasma Glucose in Mice" Science (2012) vol. 336, pp. 604-608.

Stanley et al., "Remote regulation of glucose homeostasis in mice using genetically encoded nanoparticles" Nature Medicine (2015) vol. 21, No. 1, pp. 92-98, plus additional materials including corrigendum (29 pages total).

St-Pierre et al., "High-fidelity optical reporting of neuronal electrical activity with an ultrafast fluorescent voltage sensor." Nature Neuroscience (2014) vol. 17, No. 6, pp. 884-889.

Szobota et al., "Remote control of neuronal activity with a light-gated glutamate receptor" Neuron (2007) vol. 54, No. 4, pp. 535-545.

Torti et al., "Human H-kininogen is a Ferritin-binding Protein" Journal of Biological Chemistry (1998) vol. 273, No. 22, pp. 13630-13635.

Tosha et al., "Ferritin Protein Nanocage Ion Channels" Journal of Biological Chemistry (2012) vol. 287, No. 16, pp. 13016-13025.

Wachter et al., "Sensitivity of the yellow variant of green fluorescent protein to halides and nitrate." Current Biology (1999) vol. 9, No. 17, pp. R628-R629.

Wilkinson et al., "Tissue-specific expression of ferritin H regulates cellular iron homoeostasis in vivo." Biochemical Journal (2006) vol. 395, No. 3, pp. 501-507.

Zemelman et al., "Selective photostimulation of genetically chARGed neurons" Neuron (2002) vol. 33, No. 1, pp. 15-22.

Zhang et al., "Temperature-sensitive TREK currents contribute to setting the resting membrane potential in embryonic atrial myocytes." J Physiol (2008) vol. 586(Pt 15), No. 3645-3656.

FIG. 9a-d
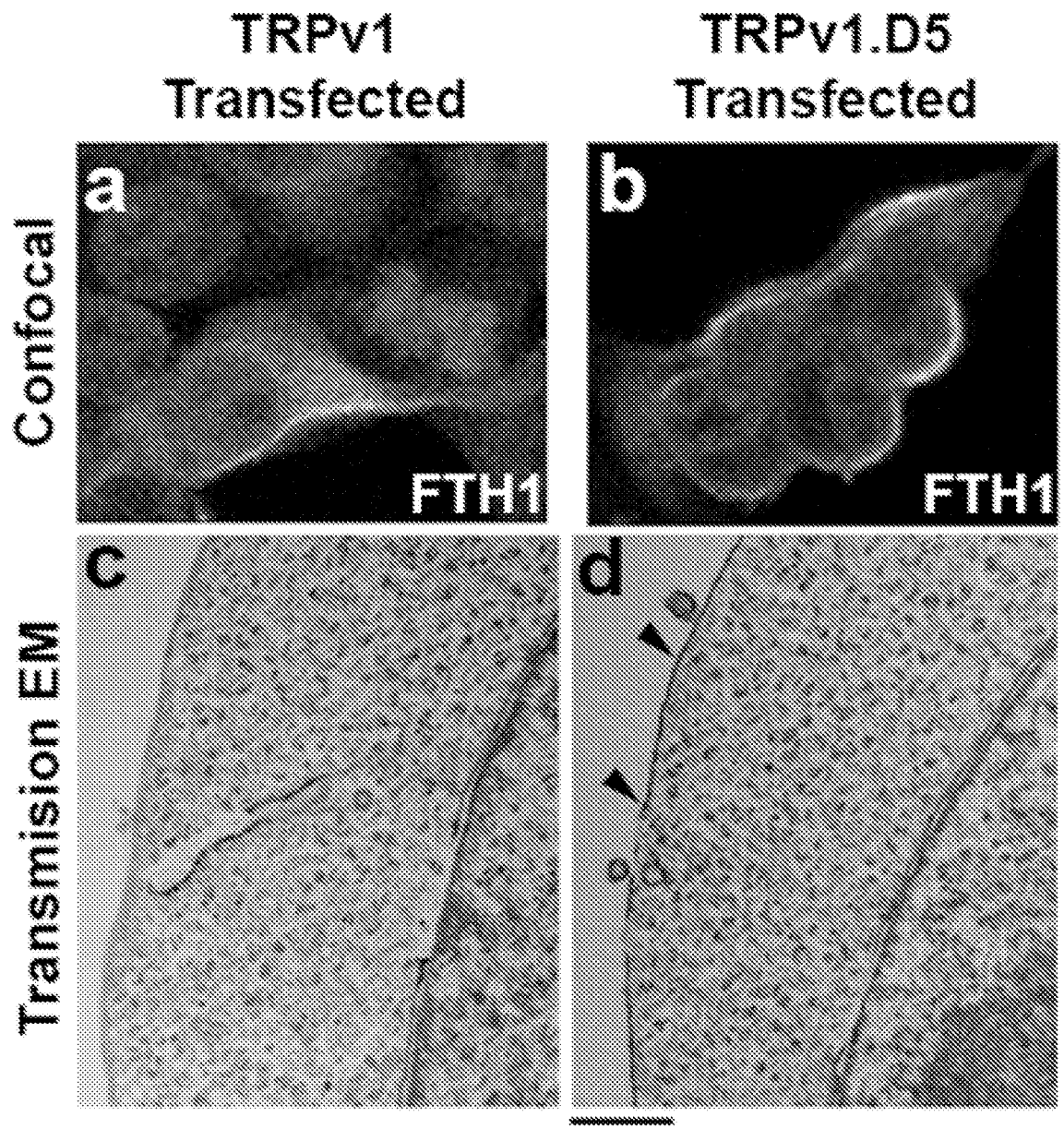

FIG. 15a-d
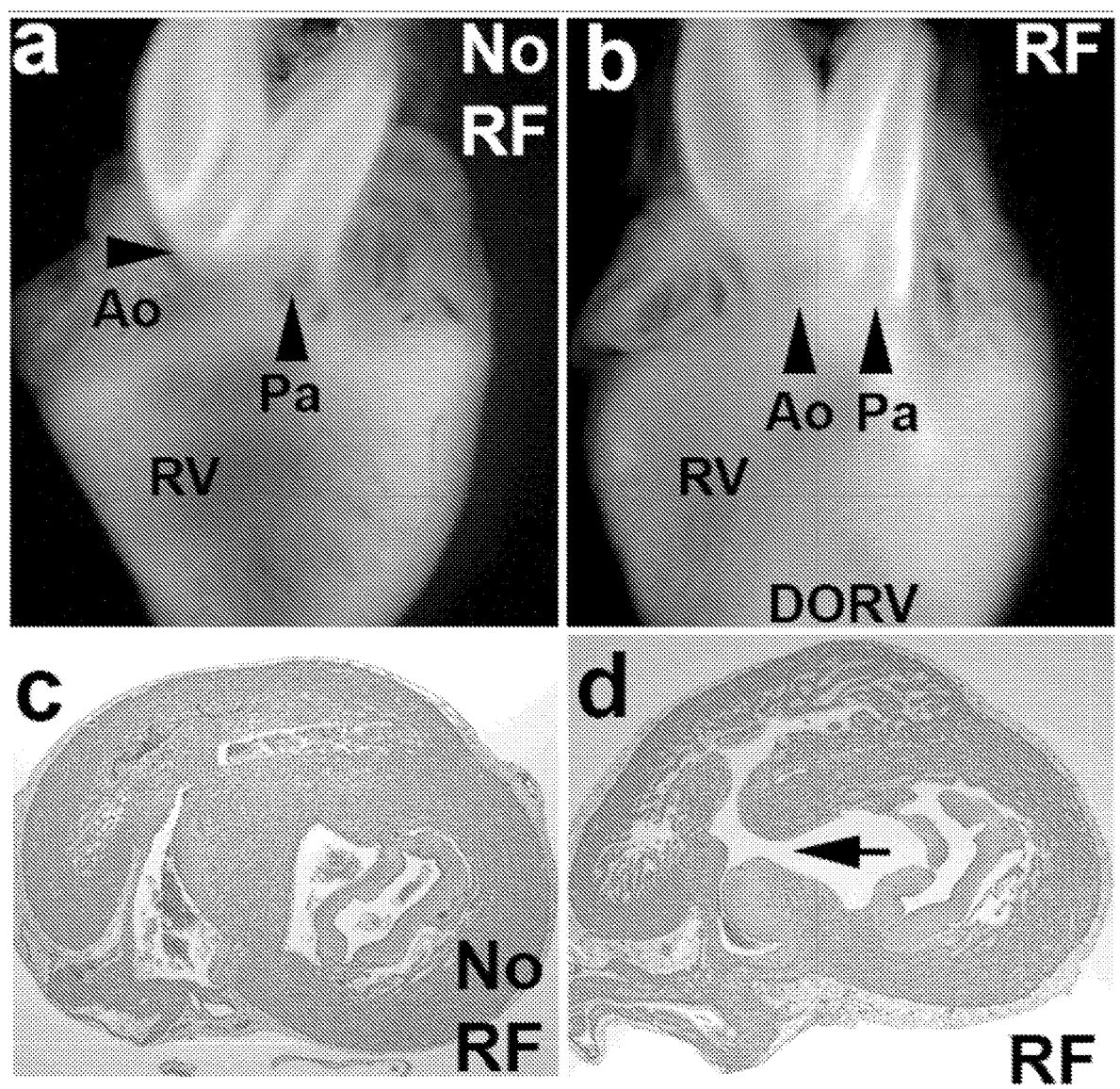

SEQUENCE LISTING

```
<160> NUMBER OF SEQ ID NOS: 20

<210> SEQ ID NO 1
<211> LENGTH: 2904
<212> TYPE: DNA
<213> ORGANISM: Artificial Sequence
<220> FEATURE:
<223> OTHER INFORMATION: mouse/human chimera TRPv1.D5

<400> SEQUENCE: 1
atggagaaat gggctagctt agactcggat gaatctgagc ccccagccca agagaactcc      60
tgcccggacc ctccagacag agaccctaac tccaagccgc ctccagccaa gccccacatc     120
tttgctacca ggagtcgcac ccggcttttt gggaagggtg actcagaaga ggcctctccc     180
atggactgcc cttatgagga aggcgggctg gcctcctgcc ctatcatcac cgtcagctct     240
gttgtcactc tccagaggtc tgtggatgga cctacctgtc tcaggcagac atcccaggac     300
tctgtctcca ctggtgttga gacgccccca aggctctatg atcgcaggag catcttcgac     360
gctgtggctc agagcaactg ccaggagctg gagagcctgc tgtccttcct gcagaagagc     420
aagaagcgcc tgactgacag cgagttcaaa gacccagaga cgggaaagac ctgtctgctc     480
aaagccatgc tcaatctgca caatgggcag aacgacacca ttgctctgct cctggacatt     540
```

| | |
|---|---|
| gcccggaaga cagatagcct gaagcagttt gtcaatgcca gctacacaga cagctactac | 600 |
| aagggccaga cagcattaca cattgccatt gaaaggcgga acatggcact ggtgaccctc | 660 |
| ttggtggaga atggagcaga tgtccaggct gctgctaacg gggacttctt caagaaaacc | 720 |
| aaagggaggc ctggcttcta ctttggtgag ctgcccctgt ccctggctgc gtgcaccaac | 780 |
| cagctggcca ttgtgaagtt cctgctgcag aactcctggc agcctgcaga catcagtgca | 840 |
| cgggattcgg tgggcaacac ggtgctgcac gcccttgtgg aggtggcaga taacacagct | 900 |
| gacaacacca agttcgtgac aaacatgtac aacgagatcc tgatcctggg ggccaaactc | 960 |
| caccccacac tgaagctaga agaactcacc aacaagaagg gcttacacc gctggctctg | 1020 |
| gctgccagca gtgggaagat tggggtcttg gcctacattc tccagaggga gatccacgaa | 1080 |
| ccagagtgcc ggcacctgtc caggaagttc actgaatggg cctatgggcc cgtgcactcc | 1140 |
| tccctttatg acctgtcctg cattgacacc tgtgagaaga attcagtgct ggaggtgatc | 1200 |
| gcctacagta gcagtgagac ccccaaccgc cacgacatgc ttctcgtgga gcccttgaac | 1260 |
| cgactcctgc aggacaagtg ggacagattt gtcaagcgca tcttctactt caacttcttc | 1320 |
| gtctactgct tgtatatgat catcttcacc acggctgctt actatcggcc tgtggaaggc | 1380 |
| ttgccccct ataagctgaa taacaccgtt ggggactatt ccgtgtcac tggagagatc | 1440 |
| ctgtctgtgt caggaggagt ctacttcttc ttccgaggga tccagtattt cctgcagagg | 1500 |
| cgaccatccc tcaagagttt gtttgtggac agctacagtg agatacttt ctttgtacag | 1560 |
| tcactgttca tgctggtgtc tgtggtactg tacttcagcc atcgcaagga gtatgtggct | 1620 |
| tccatggtgt tctccctggc catgggctgg accaacatgc tctactacac ccgaggattc | 1680 |
| cagcagatgg gcatctatgc tgtcatgatt gagaagatga tcctcagaga cctgtgtcgg | 1740 |
| tttatgttcg tctacctcgt gttcttgttt ggattttcca cagccgtagt gacactgatc | 1800 |
| gaggatggga agaataactc actgcctgtg gagtccccac cacacaagtg tcggggatct | 1860 |
| gcctgcaggc caggtaactc ttacaacagc ctgtattcca catgtctgga gctgttcaag | 1920 |
| ttcaccatcg gcatgggtga cctggagttc accgagaact atgacttcaa ggctgtcttc | 1980 |
| atcatcctgt tactgccta tgtgattctc acctacatcc tcctgctcaa catgctcatt | 2040 |
| gctctcatgg gcgagactgt caacaagatt gcacaagaga gcaagaacat ctggaagctg | 2100 |
| cagcgagcca tcaccatcct ggatacagag aagagtttcc tgaagtgcat gaggaaggcc | 2160 |
| ttccgctccg gcaagctgct gcaggtgggg ttcacgccgg acggcaagga tgacttccgg | 2220 |
| tggtgcttca gggtggatga ggtgaactgg actacctgga acaccaacgt gggcatcatc | 2280 |
| aacgaggacc caggcaactg tgagggcgtc aagcgcaccc tgagcttctc cctgcggtca | 2340 |
| ggccgagttt cagggagaaa ctggaagaac tttgccctgg ttccccttct gagggacgca | 2400 |
| agcactcgag ataggcatag cacccagccg gaagaagttc agctgaagca ctatacggga | 2460 |
| tcccttaagc cagaggatgc tgaggtcttc aaggattcca tggccccagg ggagaagtgt | 2520 |
| tctagagtaa gtccacccca cacttccatg gcacctgcac aagatgaaga gcgggattca | 2580 |
| ggaaaagaac aagggcatac tcgtagacat gactgggggcc atgaaaaaca aagaaaacat | 2640 |
| aatcttggcc atggccataa acatgaacgt gaccaagggc atgggcacca agaggacat | 2700 |
| ggccttggcc atggacacga acaacagcat ggtcttggtc atggacataa gttcaaactt | 2760 |
| gatgatgatc ttgaacacca agggggccat gtccttgacc atggacataa gcataagcat | 2820 |
| ggtcatggcc acgaaaaaca taaaaataaa ggcaaaaaga atggaaagca caatggttgg | 2880 |
| aaaacagagc atttggcaag cttg | 2904 |

<210> SEQ ID NO 2
<211> LENGTH: 968
<212> TYPE: PRT
<213> ORGANISM: Artificial Sequence
<220> FEATURE:
<223> OTHER INFORMATION: mouse/human chimera TRPv1.D5

<400> SEQUENCE: 2

```
Met Glu Lys Trp Ala Ser Leu Asp Ser Asp Glu Ser Glu Pro Pro Ala
1               5                   10                  15

Gln Glu Asn Ser Cys Pro Asp Pro Asp Arg Asp Pro Asn Ser Lys
            20                  25                  30

Pro Pro Pro Ala Lys Pro His Ile Phe Ala Thr Arg Ser Arg Thr Arg
            35                  40                  45

Leu Phe Gly Lys Gly Asp Ser Glu Glu Ala Ser Pro Met Asp Cys Pro
    50                  55                  60

Tyr Glu Glu Gly Gly Leu Ala Ser Cys Pro Ile Ile Thr Val Ser Ser
65                  70                  75                  80

Val Val Thr Leu Gln Arg Ser Val Asp Gly Pro Thr Cys Leu Arg Gln
                85                  90                  95

Thr Ser Gln Asp Ser Val Ser Thr Gly Val Glu Thr Pro Pro Arg Leu
            100                 105                 110

Tyr Asp Arg Arg Ser Ile Phe Asp Ala Val Ala Gln Ser Asn Cys Gln
        115                 120                 125

Glu Leu Glu Ser Leu Leu Ser Phe Leu Gln Lys Ser Lys Lys Arg Leu
    130                 135                 140

Thr Asp Ser Glu Phe Lys Asp Pro Glu Thr Gly Lys Thr Cys Leu Leu
145                 150                 155                 160

Lys Ala Met Leu Asn Leu His Asn Gly Gln Asn Asp Thr Ile Ala Leu
                165                 170                 175

Leu Leu Asp Ile Ala Arg Lys Thr Asp Ser Leu Lys Gln Phe Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala Ala Asn Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Ala Ile Val Lys Phe Leu Leu Gln Asn Ser
            260                 265                 270

Trp Gln Pro Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Asn Met Tyr Asn Glu Ile Leu Ile Leu Gly Ala Lys Leu
305                 310                 315                 320

His Pro Thr Leu Lys Leu Glu Glu Leu Thr Asn Lys Lys Gly Leu Thr
                325                 330                 335

Pro Leu Ala Leu Ala Ala Ser Ser Gly Lys Ile Gly Val Leu Ala Tyr
            340                 345                 350

Ile Leu Gln Arg Glu Ile His Glu Pro Glu Cys Arg His Leu Ser Arg
        355                 360                 365
```

-continued

```
Lys Phe Thr Glu Trp Ala Tyr Gly Pro Val His Ser Ser Leu Tyr Asp
    370                 375                 380
Leu Ser Cys Ile Asp Thr Cys Glu Lys Asn Ser Val Leu Glu Val Ile
385                 390                 395                 400
Ala Tyr Ser Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
            420                 425                 430
Arg Ile Phe Tyr Phe Asn Phe Val Tyr Cys Leu Tyr Met Ile Ile
        435                 440                 445
Phe Thr Thr Ala Ala Tyr Tyr Arg Pro Val Glu Gly Leu Pro Pro Tyr
450                 455                 460
Lys Leu Asn Asn Thr Val Gly Asp Tyr Phe Arg Val Thr Gly Glu Ile
465                 470                 475                 480
Leu Ser Val Ser Gly Val Tyr Phe Phe Arg Gly Ile Gln Tyr
                485                 490                 495
Phe Leu Gln Arg Arg Pro Ser Leu Lys Ser Leu Phe Val Asp Ser Tyr
                500                 505                 510
Ser Glu Ile Leu Phe Phe Val Gln Ser Leu Phe Met Leu Val Ser Val
            515                 520                 525
Val Leu Tyr Phe Ser His Arg Lys Glu Tyr Val Ala Ser Met Val Phe
    530                 535                 540
Ser Leu Ala Met Gly Trp Thr Asn Met Leu Tyr Tyr Thr Arg Gly Phe
545                 550                 555                 560
Gln Gln Met Gly Ile Tyr Ala Val Met Ile Glu Lys Met Ile Leu Arg
                565                 570                 575
Asp Leu Cys Arg Phe Met Phe Val Tyr Leu Val Phe Leu Phe Gly Phe
            580                 585                 590
Ser Thr Ala Val Val Thr Leu Ile Glu Asp Gly Lys Asn Asn Ser Leu
        595                 600                 605
Pro Val Glu Ser Pro His Lys Cys Arg Gly Ser Ala Cys Arg Pro
610                 615                 620
Gly Asn Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
        675                 680                 685
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Phe Thr Pro Asp Gly Lys
                725                 730                 735
Asp Asp Phe Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Gly Arg Val Ser
770                 775                 780
```

| | | | | | | | | | | | | | | |
|---|---|---|---|---|---|---|---|---|---|---|---|---|---|---|
|Gly|Arg|Asn|Trp|Lys|Asn|Phe|Ala|Leu|Val|Pro|Leu|Leu|Arg|Asp|Ala|
|785| | | |790| | | |795| | | |800| | |

Ser Thr Arg Asp Arg His Ser Thr Gln Pro Glu Glu Val Gln Leu Lys
            805                 810                 815

His Tyr Thr Gly Ser Leu Lys Pro Glu Asp Ala Glu Val Phe Lys Asp
            820                 825                 830

Ser Met Ala Pro Gly Glu Lys Cys Ser Arg Val Ser Pro Pro His Thr
        835                 840                 845

Ser Met Ala Pro Ala Gln Asp Glu Glu Arg Asp Ser Gly Lys Glu Gln
        850                 855                 860

Gly His Thr Arg Arg His Asp Trp Gly His Glu Lys Gln Arg Lys His
865                 870                 875                 880

Asn Leu Gly His Gly His Lys His Glu Arg Asp Gln Gly His Gly His
                885                 890                 895

Gln Arg Gly His Gly Leu Gly His Gly His Glu Gln Gln His Gly Leu
                900                 905                 910

Gly His Gly His Lys Phe Lys Leu Asp Asp Asp Leu Gly His Gln Gly
            915                 920                 925

Gly His Val Leu Asp His Gly His Lys His Lys His Gly His Gly His
        930                 935                 940

Gly Lys His Lys Asn Lys Gly Lys Lys Asn Gly Lys His Asn Gly Trp
945                 950                 955                 960

Lys Thr Glu His Leu Ala Ser Leu
            965

```
<210> SEQ ID NO 3
<211> LENGTH: 2904
<212> TYPE: DNA
<213> ORGANISM: Artificial Sequence
<220> FEATURE:
<223> OTHER INFORMATION: human TRPv1.D5

<400> SEQUENCE: 3
atgaagaaat ggagcagcac agacttgggg gcagctgcgg acccactcca aaaggacacc      60
tgcccagacc ccctggatgg agaccctaac tccaggccac ctccagccaa gcccagctc     120 tccacggcca agagccgcac ccggctcttt gggaagggtg actcggagga ggctttcccg     180
gtggattgcc ctcacgagga aggtgagctg gactcctgcc cgaccatcac agtcagccct     240
gttatcacca tccagaggcc aggagacggc cccaccggtg ccaggctgct gtcccaggac     300
tctgtcgccg ccagcaccga gaagaccctc aggctctatg atcgcaggag tatctttgaa     360
gccgttgctc agaataactg ccaggatctg gagagcctgc tgctcttcct gcagaagagc     420
aagaagcacc tcacagacaa cgagttcaaa gaccctgaga cagggaagac ctgtctgctg     480
aaagccatgc tcaacctgca cgacggacag aacaccacca tcccctgct cctggagatc     540 gcgcggcaaa cggacagcct gaaggagctt gtcaacgcca gctacacgga cagctactac     600
aagggccaga cagcactgca catcgccatc gagagacgca cagtggccct ggtgaccctc     660
ctggtggaga acgagcaga cgtccaggct gcggcccatg gggacttctt taagaaaacc     720
aaagggcggc tggattcta cttcggtgaa ctgcccctgt ccctggccgc gtgcaccaac     780
cagctgggca tcgtgaagtt cctgctgcag aactcctggc agacggccga catcagcgcc     840
agggactcgg tgggcaacac ggtgctgcac gccctggtgg aggtggccga caacacggcc     900
gacaacacga agtttgtgac gagcatgtac aatgagattc tgatgctggg ggccaaactg     960
caccccgacg ctgaagctgg aggagctcacc aacaagaagg gaatgacgcc gctggctctg    1020
```

-continued

```
gcagctggga ccgggaagat cggggtcttg gcctatattc tccagcggga gatccaggag    1080
cccgagtgca ggcacctgtc caggaagttc accgagtggg cctacgggcc cgtgcactcc    1140
tcgctgtacg acctgtcctg catcgacacc tgcgagaaga actcggtgct ggaggtgatc    1200
gcctacagca gcagcgagac ccctaatcgc cacgacatgc tcttggtgga ccgctgaac    1260 cgactcctgc aggacaagtg ggacagattc gtcaagcgca tcttctactt caacttcctg    1320
gtctactgcc tgtacatgat catcttcacc atggctgcct actacaggcc cgtggatggc    1380
ttgcctccct ttaagatgga aaaaactgga gactatttcc gagttactgg agagatcctg    1440
tctgtgttag gaggagtcta cttcttttc cgagggattc agtatttcct gcagaggcgg    1500
ccgtcgatga agaccctgtt tgtggacagc tacagtgaga tgcttttctt tctgcagtca    1560
ctgttcatgc tggccaccgt ggtgctgtac ttcagccacc tcaaggagta tgtggcttcc    1620
atggtattct ccctggcctt gggctggacc aacatgctct actacacccg cggtttccag    1680
cagatgggca tctatgccgt catgatagag aagatgatcc tgagagacct gtgccgtttc    1740
atgtttgtct acatcgtctt cttgttcggg ttttccacag cggtggtgac gctgattgaa    1800
gacgggaaga tgactcccct gccgtctgag tccacgtcgc acaggtggcg ggggcctgcc    1860
tgcaggcccc ccgatagctc ctacaacagc ctgtactcca cctgcctgga gctgttcaag    1920
ttcaccatcg gcatgggcga cctggagttc actgagaact atgacttcaa ggctgtcttc    1980
atcatcctgc tgctggccta tgtaattctc acctacatcc tcctgctcaa catgctcatc    2040
gccctcatgg gtgagactgt caacaagatc gcacaggaga gcaagaacat ctggaagctg    2100
cagagagcca tcaccatcct ggacacggag aagagcttcc ttaagtgcat gaggaaggcc    2160
ttccgctcag gcaagctgct gcaggtgggg tacacacctg atggcaagga cgactaccgg    2220
tggtgcttca gggtggacga ggtgaactgg accacctgga acaccaacgt gggcatcatc    2280
aacgaagacc cgggcaactg tgagggcgtc aagcgcaccc tgagcttctc cctgcggtca    2340
agcagagttt caggcagaca ctggaagaac tttgccctgg tccccctttt aagagaggca    2400
agtgctcgag ataggcagtc tgctcagccc gaggaagttt atctgcgaca gttttcaggg    2460
tctctgaagc cagaggacgc tgaggtcttc aagagtcctg ccgcttccgg ggagaagtgg    2520
tctagagtaa gtccacccca cacttccatg gcacctgcac aagatgaaga gcgggattca    2580
ggaaaagaac aagggcatac tcgtagacat gactggggcc atgaaaaaca agaaaaacat    2640
aatcttggcc atggccataa acatgaacgt gaccaagggc atgggcacca agaggacat    2700 ggccttggcc atggacacga caacagcat ggtcttggtc atggacataa gttcaaactt    2760
gatgatgatc ttgaacacca aggggccat gtccttgacc atggacataa gcataagcat    2820
ggtcatggcc acgaaaaaca taaaaataaa ggcaaaaaga atggaaagca caatggttgg    2880
aaaacagagc atttggcaag cttg                                           2904
```

<210> SEQ ID NO 4
<211> LENGTH: 968
<212> TYPE: PRT
<213> ORGANISM: Artificial Sequence
<220> FEATURE:
<223> OTHER INFORMATION: human TRPV1.D5

<400> SEQUENCE: 4

Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
            20                  25                  30

-continued

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
 50                  55                  60

His Glu Glu Gly Glu Leu Asp Ser Cys Pro Thr Ile Thr Val Ser Pro
 65                      70                  75                  80

Val Ile Thr Ile Gln Arg Pro Gly Asp Gly Pro Thr Gly Ala Arg Leu
                 85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
            115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
    195                 200                 205

Ala Ile Glu Arg Arg Asn Met Ala Leu Val Thr Leu Leu Val Glu Asn
210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
    275                 280                 285

Leu His Ala Leu Val Glu Val Ala Asp Asn Thr Ala Asp Asn Thr Lys
290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
    355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
    435                 440                 445

```
Phe Thr Met Ala Ala Tyr Tyr Arg Pro Val Asp Gly Leu Pro Pro Phe
450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                485                 490                 495
Leu Gln Arg Arg Pro Ser Met Lys Thr Leu Phe Val Asp Ser Tyr Ser
                500                 505                 510
Glu Met Leu Phe Phe Leu Gln Ser Leu Phe Met Leu Ala Thr Val Val
            515                 520                 525
Leu Tyr Phe Ser His Leu Lys Glu Tyr Val Ala Ser Met Val Phe Ser
530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
                580                 585                 590
Thr Ala Val Val Thr Leu Ile Glu Asp Gly Lys Asn Asp Ser Leu Pro
            595                 600                 605
Ser Glu Ser Thr Ser His Arg Trp Arg Gly Pro Ala Cys Arg Pro Pro
            610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
                660                 665                 670
Ile Leu Leu Leu Asn Met Leu Ile Ala Leu Met Gly Glu Thr Val Asn
                675                 680                 685
Lys Ile Ala Gln Glu Ser Lys Asn Ile Trp Lys Leu Gln Arg Ala Ile
690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
                740                 745                 750
Trp Asn Thr Asn Val Gly Ile Ile Asn Glu Asp Pro Gly Asn Cys Glu
            755                 760                 765
Gly Val Lys Arg Thr Leu Ser Phe Ser Leu Arg Ser Ser Arg Val Ser
            770                 775                 780
Gly Arg His Trp Lys Asn Phe Ala Leu Val Pro Leu Leu Arg Glu Ala
            785                 790                 795                 800
Ser Ala Arg Asp Arg Gln Ser Ala Gln Pro Glu Val Tyr Leu Arg
                805                 810                 815
Gln Phe Ser Gly Ser Leu Lys Pro Glu Asp Ala Glu Val Phe Lys Ser
                820                 825                 830
Pro Ala Ala Ser Gly Glu Lys Trp Ser Arg Val Ser Pro Pro His Thr
            835                 840                 845
Ser Met Ala Pro Ala Gln Asp Glu Glu Arg Asp Ser Gly Lys Glu Gln
850                 855                 860
```

```
Gly His Thr Arg Arg His Asp Trp Gly His Glu Lys Gln Arg Lys His
865                 870                 875                 880

Asn Leu Gly His Gly His Lys His Glu Arg Asp Gln Gly His Gly His
                885                 890                 895

Gln Arg Gly His Gly Leu Gly His Gly His Glu Gln Gln His Gly Leu
            900                 905                 910

Gly His Gly His Lys Phe Lys Leu Asp Asp Asp Leu Glu His Gln Gly
        915                 920                 925

Gly His Val Leu Asp His Gly His Lys His Lys His Gly His Gly His
    930                 935                 940

Gly Lys His Lys Asn Lys Gly Lys Lys Asn Gly Lys His Asn Gly Trp
945                 950                 955                 960

Lys Thr Glu His Leu Ala Ser Leu
                965
```

<210> SEQ ID NO 5
<211> LENGTH: 3237
<212> TYPE: DNA
<213> ORGANISM: Artificial Sequence
<220> FEATURE:
<223> OTHER INFORMATION: D5.ANO1 human mouse chimera

<400> SEQUENCE: 5

```
atggcacctg cacaagatga agagcgggat tcaggaaaag aacaagggca tactcgtaga      60
catgactggg gccatgaaaa acaaagaaaa cataatcttg ccatggccca taaacatgaa     120
cgtgaccaag gcatgggca ccaaagagga catggccttg ccatggaca cgaacaacag      180
catggtcttg gtcatggaca taagttcaaa cttgatgatg atcttgaaca ccaaggggc      240
catgtccttg accatggaca taagcataag catggtcatg ccacggaaa acataaaaat     300
aaaggcaaaa gaatggaaa gcacaatggt tggaaaacag agcatttggc aagcttggcg      360
gccgccacga tgagggtccc cgagaagtac tcgacgctcc cggcggagga ccgcagcgtc     420
cacatcgtga acatctgcgc catcgaggac ctgggctacc tgccgtccga gggcacgttg     480
ctgaactctc tgtccgtgga ccccgacgcc gaatgcaagt atggactata cttcagggat     540
ggcaaacgga aggtggacta catcttggta taccatcaca gagagcctc agggagcagg     600
actctggcca ggaggggact acaaaatgac atggtcctgg gaccccgcag cgtcaggcag     660
gaccagcccc ttcccgggaa ggggagccct gtggatgcag gctcaccgga agtccccatg     720
gattaccatg aagatgacaa acgcttcaga cgggaggaat atgagggcaa cctgttggag     780
gcaggcctgg agttggagaa tgacgaggat accaaaatcc atggtgtcgg gtttgtgaag     840
atccatgcgc cctggcatgt gctctgtagg gaagctgagt ttttgaaact aaagatgccc     900
acaaagaagg tgtaccacat cagtgagacg cgaggcctcc tgaaaaccat caactcggtt     960
ctgcagaaga tcacagaccc catccagccc aaggtggctg agcacaggcc acagaccaca    1020
aagaggctct cctatccctt ctcccgggag aagcaacacc tattcgacct gactgacagg    1080
gactcttttt tcgacagcaa aaccccggagc acaatagtct atgaaatcct gaagagaaca    1140
acgtgcacca aggccaagta cagcatgggg atcaccagcc tcctggccaa tggcgtatac    1200
tcagctgcat accctctgca cgatggggac tatgagggtg acaacgttga gttcaacgac    1260
aggaaactcc tgtatgagga tgggcaagtt tacggagtct tctacaaata ccagcccatt    1320
gacctggtca ggaaatactt tggtgagaag gttggcctgt actttgcctg cttggagcc    1380
tacacccaga tgctcatccc tgcctcgatc gtgggtgtca ttgtctttct ctatggatgt    1440
```

```
gccactgtgg acgaaaacat ccccagtatg gagatgtgtg accagagata caacatcacc    1500
atgtgtcctc tgtgtgacaa gacctgcagc tactggaaga tgagctcagc ctgtgccaca    1560
gcccgtgcca gtcacctttt tgataaccct gccaccgtct tcttctctgt gtttatggcc    1620
ctctgggctg ccactttcat ggagcactgg aaacggaagc agatgaggct caactaccga    1680
tgggacctca caggcttcga ggaggaggag gatcatccca gagcagagta tgaagccaga    1740
gtcttagaga agtcactgag aaaagaatcc agaaacaaag agaccgacaa ggtgaagctg    1800
acctggaggg accgattccc agcctatttc accaatcttg tctccatcat cttcatgatc    1860
gcagtgacat ttgcaatcgt cctcggagtt atcatctata gaatctccac agctgcagcc    1920
ttggccatga actcctcccc gtctgtgcgg tccaacatcc gggttacagt cacggccacc    1980
gctgttatca tcaacctcgt ggtcatcatt ctgctggatg aagtttacgg ctgcattgcc    2040
aggtggctca ccaagattga ggtcccaaag acagagaaga gctttgagga gaggctaacc    2100
ttcaaggcct tcctgctcaa gtttgtgaac tcttacactc ccatcttcta tgtcgccttc    2160
ttcaaaggcc ggtttgttgg tcggcccggt gactacgtgt acatcttccg ctctttccgg    2220
atggaggagt gtgccccggg cggctgcctc atggagctct gtatccagct gagcatcatt    2280
atgctgggca agcagctaat ccagaacaat ctcttcgaga ttggcatccc gaagatgaaa    2340
aagttcatcc gctacctgaa gctgcgcaga cagagcccct cagaccgtga agagtacgtg    2400
aagcggaagc agcgctatga ggtggacttc aacctcgaac ctttcgccgg cctcacgccc    2460
gagtacatgg aaatgatcat tcagttcggc tttgtcaccc tgtttgttgc gtccttccct    2520
ctggctccac tcttcgccct gctaaacaac atcattgaga tccgcctgga tgccaaaaag    2580
tttgtcaccg agctacggag gccagtagcc atcagagcca agacatcgg catctggtat    2640
aacatcctca gaggtgttgg gaagctggct gtcatcatta atgcctttgt gatctccttc    2700
acgtctgact tcatccctcg cctggtgtac ctctacatgt acagtcagaa tgggaccatg    2760
cacggcttcg tcaatcacac gctctcttcc ttcaatgtca gcgacttcca gaatggcaca    2820
gcacccaatg acccactgga cctgggctat gaggttcaga tctgcaggta taagagttac    2880
cgggaacccc catggtcaga acacaagtat gacatctcca aagacttctg gctgtcctg    2940
gccgcccgac tggcatttgt cattgtcttc cagaacctgg tgatgttcat gagtgacttt    3000
gtggactggg tgatccctga tatccccaaa gacatcagcc agcagatcca aaagagaag    3060
gttctcatgg tggagctgtt tatgcgtgag agcagggca agcagcagct actggacaca    3120
tggatggaga aggagaagcc aagggatgtg ccttgtaaca accacagccc cacaacccac    3180
ccagaggcag gcgacggcag cccagtcccc agctacgagt accatgggga cgcgctg     3237
```

<210> SEQ ID NO 6
<211> LENGTH: 1079
<212> TYPE: PRT
<213> ORGANISM: Artificial Sequence
<220> FEATURE:
<223> OTHER INFORMATION: D5.ANO1 human mouse chimera

<400> SEQUENCE: 6

Met Ala Pro Ala Gln Asp Glu Glu Arg Asp Ser Gly Lys Glu Gln Gly
1               5                   10                  15

His Thr Arg Arg His Asp Trp Gly His Glu Lys Gln Arg Lys His Asn
            20                  25                  30

Leu Gly His Gly His Lys His Glu Arg Asp Gln Gly His Gly His Gln
        35                  40                  45

-continued

```
Arg Gly His Gly Leu Gly His Gly His Glu Gln Gln His Gly Leu Gly
 50                  55                  60
His Gly His Lys Phe Lys Leu Asp Asp Leu Glu His Gln Gly Gly
 65                  70                  75                  80
His Val Leu Asp His Gly His Lys His Gly His Gly His Gly
                 85                  90                  95
Lys His Lys Asn Lys Gly Lys Lys Asn Gly Lys His Asn Gly Trp Lys
                100                 105                 110
Thr Glu His Leu Ala Ser Leu Ala Ala Thr Met Arg Val Pro Glu
                115                 120                 125
Lys Tyr Ser Thr Leu Pro Ala Glu Asp Arg Ser Val His Ile Val Asn
130                 135                 140
Ile Cys Ala Ile Glu Asp Leu Gly Tyr Leu Pro Ser Glu Gly Thr Leu
145                 150                 155                 160
Leu Asn Ser Leu Ser Val Asp Pro Asp Ala Glu Cys Lys Tyr Gly Leu
                165                 170                 175
Tyr Phe Arg Asp Gly Lys Arg Lys Val Asp Tyr Ile Leu Val Tyr His
                180                 185                 190
His Lys Arg Ala Ser Gly Ser Arg Thr Leu Ala Arg Arg Gly Leu Gln
                195                 200                 205
Asn Asp Met Val Leu Gly Thr Arg Ser Val Arg Gln Asp Gln Pro Leu
210                 215                 220
Pro Gly Lys Gly Ser Pro Val Asp Ala Gly Ser Pro Glu Val Pro Met
225                 230                 235                 240
Asp Tyr His Glu Asp Asp Lys Arg Phe Arg Arg Glu Glu Tyr Glu Gly
                245                 250                 255
Asn Leu Leu Glu Ala Gly Leu Glu Leu Glu Asn Asp Glu Asp Thr Lys
                260                 265                 270
Ile His Gly Val Gly Phe Val Lys Ile His Ala Pro Trp His Val Leu
                275                 280                 285
Cys Arg Glu Ala Glu Phe Leu Lys Leu Lys Met Pro Thr Lys Lys Val
290                 295                 300
Tyr His Ile Ser Glu Thr Arg Gly Leu Leu Lys Thr Ile Asn Ser Val
305                 310                 315                 320
Leu Gln Lys Ile Thr Asp Pro Ile Gln Pro Lys Val Ala Glu His Arg
                325                 330                 335
Pro Gln Thr Thr Lys Arg Leu Ser Tyr Pro Phe Ser Arg Glu Lys Gln
                340                 345                 350
His Leu Phe Asp Leu Thr Asp Arg Asp Ser Phe Phe Asp Ser Lys Thr
                355                 360                 365
Arg Ser Thr Ile Val Tyr Glu Ile Leu Lys Arg Thr Thr Cys Thr Lys
370                 375                 380
Ala Lys Tyr Ser Met Gly Ile Thr Ser Leu Leu Ala Asn Gly Val Tyr
385                 390                 395                 400
Ser Ala Ala Tyr Pro Leu His Asp Gly Asp Tyr Glu Gly Asp Asn Val
                405                 410                 415
Glu Phe Asn Asp Arg Lys Leu Leu Tyr Glu Glu Trp Ala Ser Tyr Gly
                420                 425                 430
Val Phe Tyr Lys Tyr Gln Pro Ile Asp Leu Val Arg Lys Tyr Phe Gly
                435                 440                 445
Glu Lys Val Gly Leu Tyr Phe Ala Trp Leu Gly Ala Tyr Thr Gln Met
450                 455                 460
```

-continued

```
Leu Ile Pro Ala Ser Ile Val Gly Val Ile Val Phe Leu Tyr Gly Cys
465                 470                 475                 480

Ala Thr Val Asp Glu Asn Ile Pro Ser Met Glu Met Cys Asp Gln Arg
                485                 490                 495

Tyr Asn Ile Thr Met Cys Pro Leu Cys Asp Lys Thr Cys Ser Tyr Trp
                500                 505                 510

Lys Met Ser Ser Ala Cys Ala Thr Ala Arg Ala Ser His Leu Phe Asp
            515                 520                 525

Asn Pro Ala Thr Val Phe Phe Ser Val Phe Met Ala Leu Trp Ala Ala
        530                 535                 540

Thr Phe Met Glu His Trp Lys Arg Lys Gln Met Arg Leu Asn Tyr Arg
545                 550                 555                 560

Trp Asp Leu Thr Gly Phe Glu Glu Glu Asp His Pro Arg Ala Glu
                565                 570                 575

Tyr Glu Ala Arg Val Leu Glu Lys Ser Leu Arg Lys Glu Ser Arg Asn
                580                 585                 590

Lys Glu Thr Asp Lys Val Lys Leu Thr Trp Arg Asp Arg Phe Pro Ala
            595                 600                 605

Tyr Phe Thr Asn Leu Val Ser Ile Ile Phe Met Ile Ala Val Thr Phe
        610                 615                 620

Ala Ile Val Leu Gly Val Ile Ile Tyr Arg Ile Ser Thr Ala Ala Ala
625                 630                 635                 640

Leu Ala Met Asn Ser Ser Pro Ser Val Arg Ser Asn Ile Arg Val Thr
                645                 650                 655

Val Thr Ala Thr Ala Val Ile Ile Asn Leu Val Val Ile Ile Leu Leu
        660                 665                 670

Asp Glu Val Tyr Gly Cys Ile Ala Arg Trp Leu Thr Lys Ile Glu Val
            675                 680                 685

Pro Lys Thr Glu Lys Ser Phe Glu Glu Arg Leu Thr Phe Lys Ala Phe
        690                 695                 700

Leu Leu Lys Phe Val Asn Ser Tyr Thr Pro Ile Phe Tyr Val Ala Phe
705                 710                 715                 720

Phe Lys Gly Arg Phe Val Gly Arg Pro Gly Asp Tyr Val Tyr Ile Phe
                725                 730                 735

Arg Ser Phe Arg Met Glu Glu Cys Ala Pro Gly Gly Cys Leu Met Glu
                740                 745                 750

Leu Cys Ile Gln Leu Ser Ile Ile Met Leu Gly Lys Gln Leu Ile Gln
            755                 760                 765

Asn Asn Leu Phe Glu Ile Gly Ile Pro Lys Met Lys Lys Phe Ile Arg
        770                 775                 780

Tyr Leu Lys Leu Arg Arg Gln Ser Pro Ser Asp Arg Glu Glu Tyr Val
785                 790                 795                 800

Lys Arg Lys Gln Arg Tyr Glu Val Asp Phe Asn Leu Glu Pro Phe Ala
                805                 810                 815

Gly Leu Thr Pro Glu Tyr Met Glu Met Ile Ile Gln Phe Gly Phe Val
            820                 825                 830

Thr Leu Phe Val Ala Ser Phe Pro Leu Ala Pro Leu Phe Ala Leu Leu
        835                 840                 845

Asn Asn Ile Ile Glu Ile Arg Leu Asp Ala Lys Lys Phe Val Thr Glu
        850                 855                 860

Leu Arg Arg Pro Val Ala Ile Arg Ala Lys Asp Ile Gly Ile Trp Tyr
865                 870                 875                 880
```

```
Asn Ile Leu Arg Gly Val Gly Lys Leu Ala Val Ile Asn Ala Phe
            885                 890                 895

Val Ile Ser Phe Thr Ser Asp Phe Ile Pro Arg Leu Val Tyr Leu Tyr
        900                 905                 910

Met Tyr Ser Gln Asn Gly Thr Met His Gly Phe Val Asn His Thr Leu
        915                 920                 925

Ser Ser Phe Asn Val Ser Asp Phe Gln Asn Gly Thr Ala Pro Asn Asp
    930                 935                 940

Pro Leu Asp Leu Gly Tyr Glu Val Gln Ile Cys Arg Tyr Lys Asp Tyr
945                 950                 955                 960

Arg Glu Pro Pro Trp Ser Glu His Lys Tyr Asp Ile Ser Lys Asp Phe
                965                 970                 975

Trp Ala Val Leu Ala Ala Arg Leu Ala Phe Val Ile Val Phe Gln Asn
                980                 985                 990

Leu Val Met Phe Met Ser Asp Phe  Val Asp Trp Val Ile  Pro Asp Ile
                995                 1000                1005

Pro Lys  Asp Ile Ser Gln Gln   Ile His Lys Glu Lys  Val Leu Met
    1010                1015                    1020

Val Glu  Leu Phe Met Arg Glu   Glu Gln Gly Lys Gln   Gln Leu Leu
    1025                1030                    1035

Asp Thr  Trp Met Glu Lys Glu   Lys Pro Arg Asp Val   Pro Cys Asn
    1040                1045                    1050

Asn His  Ser Pro Thr Thr His   Pro Glu Ala Gly Asp   Gly Ser Pro
    1055                1060                    1065

Val Pro  Ser Tyr Glu Tyr His   Gly Asp Ala Leu
    1070                1075

<210> SEQ ID NO 7
<211> LENGTH: 2517
<212> TYPE: DNA
<213> ORGANISM: Artificial Sequence
<220> FEATURE:
<223> OTHER INFORMATION: Mouse TRPV1

<400> SEQUENCE: 7
atggagaaat gggctagctt agactcggat gaatctgagc ccccagccca agagaactcc      60
tgcccggacc ctccagacag agaccctaac tccaagccgc tccagccaa gccccacatc     120 tttgctacca ggagtcgcac ccggcttttt gggaagggtg actcagaaga ggcctctccc     180
atggactgcc ttatgagga aggcgggctg gcctcctgcc ctatcatcac cgtcagctct     240
gttgtcactc tccagaggtc tgtggatgga cctacctgtc tcaggcagac atcccaggac     300
tctgtctcca ctggtgttga cgcccccca aggctctatg atcgcaggag catcttcgac     360
gctgtggctc agagcaactg ccaggagctg gagagcctgc tgtccttcct gcagaagagc     420
aagaagcgcc tgactgacag cgagttcaaa gacccagaga cgggaaagac ctgtctgctc     480
aaagccatgc tcaatctgca caatgggcag aacgacacca ttgctctgct cctggacatt     540
gcccggaaga cagatagcct gaagcagttt gtcaatgcca gctacacaga cagctactac     600
aagggccaga cagcattaca cattgccatt gaaaggcgga acatggcact ggtgaccctc     660
ttggtggaga atgagcaga tgtccaggct gctgctaacg ggacttcttc aagaaaacc      720 aaagggaggc ctggcttcta ctttggtgag ctgcccctgt ccctggctgc gtgcaccaac     780
cagctggcca ttgtgaagtt cctgctgcag aactcctggc agcctgcaga catcagtgca     840
cgggattcgg tgggcaacac ggtgctgcac gcccttgtgg aggtggcaga taacacagct     900
```

-continued

| | |
|---|---:|
| gacaacacca agttcgtgac aaacatgtac aacgagatcc tgatcctggg ggccaaactc | 960 |
| caccccacac tgaagctaga agaactcacc aacaagaagg ggcttacacc gctggctctg | 1020 |
| gctgccagca gtgggaagat tggggtcttg cctacattc tccagaggga gatccacgaa | 1080 |
| ccagagtgcc ggcacctgtc caggaagttc actgaatggg cctatgggcc cgtgcactcc | 1140 |
| tcccttatg acctgtcctg cattgacacc tgtgagaaga attcagtgct ggaggtgatc | 1200 |
| gcctacagta gcagtgagac ccccaaccgc cacgacatgc ttctcgtgga gcccttgaac | 1260 |
| cgactcctgc aggacaagtg ggacagattt gtcaagcgca tcttctactt caacttcttc | 1320 |
| gtctactgct tgtatatgat catcttcacc acggctgctt actatcggcc tgtggaaggc | 1380 |
| ttgccccct ataagctgaa taacaccgtt ggggactatt ccgtgtcac tggagagatc | 1440 |
| ctgtctgtgt caggaggagt ctacttcttc ttccgaggga tccagtattt cctgcagagg | 1500 |
| cgaccatccc tcaagagttt gtttgtggac agctacagtg atacttttt ctttgtacag | 1560 |
| tcactgttca tgctggtgtc tgtggtactg tacttcagcc atcgcaagga gtatgtggct | 1620 |
| tccatggtgt ctccctggc catgggctgg accaacatgc tctactacac ccgaggattc | 1680 |
| cagcagatgg gcatctatgc tgtcatgatt gagaagatga tcctcagaga cctgtgtcgg | 1740 |
| tttatgttcg tctacctcgt gttcttgttt ggattttcca cagccgtagt gacactgatc | 1800 |
| gaggatggga agaataactc actgcctgtg gagtccccac cacacaagtg tcggggatct | 1860 |
| gcctgcaggc caggtaactc ttacaacagc ctgtattcca catgtctgga gctgttcaag | 1920 |
| ttcaccatcg gcatgggtga cctggagttc accgagaact atgacttcaa ggctgtcttc | 1980 |
| atcatcctgt tactggccta tgtgattctc acctacatcc tcctgctcaa catgctcatt | 2040 |
| gctctcatgg gcgagactgt caacaagatt gcacaagaga gcaagaacat ctggaagctg | 2100 |
| cagcgagcca tcaccatcct ggatacagag aagagtttcc tgaagtgcat gaggaaggcc | 2160 |
| ttccgctccg gcaagctgct gcaggtgggg ttcacgccgg acggcaagga tgacttccgg | 2220 |
| tggtgcttca gggtggatga ggtgaactgg actacctgga acaccaacgt gggcatcatc | 2280 |
| aacgaggacc caggcaactg tgagggcgtc aagcgcaccc tgagcttctc cctgcggtca | 2340 |
| ggccgagttt cagggagaaa ctggaagaac tttgccctgg ttccccttct gagggacgca | 2400 |
| agcactcgag ataggcatag cacccagccg gaagaagttc agctgaagca ctatacggga | 2460 |
| tcccttaagc cagaggatgc tgaggtcttc aaggattcca tggccccagg ggagaag | 2517 |

<210> SEQ ID NO 8
<211> LENGTH: 839
<212> TYPE: PRT
<213> ORGANISM: Artificial Sequence
<220> FEATURE:
<223> OTHER INFORMATION: Mouse TRPV1

<400> SEQUENCE: 8

Met Glu Lys Trp Ala Ser Leu Asp Ser Asp Glu Ser Glu Pro Pro Ala
1               5                   10                  15

Gln Glu Asn Ser Cys Pro Asp Pro Pro Asp Arg Asp Pro Asn Ser Lys
            20                  25                  30

Pro Pro Pro Ala Lys Pro His Ile Phe Ala Thr Arg Ser Arg Thr Arg
        35                  40                  45

Leu Phe Gly Lys Gly Asp Ser Glu Glu Ala Ser Pro Met Asp Cys Pro
    50                  55                  60

Tyr Glu Glu Gly Gly Leu Ala Ser Cys Pro Ile Ile Thr Val Ser Ser
65                  70                  75                  80

-continued

Val Val Thr Leu Gln Arg Ser Val Asp Gly Pro Thr Cys Leu Arg Gln
             85                  90                  95

Thr Ser Gln Asp Ser Val Ser Thr Gly Val Glu Thr Pro Pro Arg Leu
        100                 105                 110

Tyr Asp Arg Arg Ser Ile Phe Asp Ala Val Ala Gln Ser Asn Cys Gln
        115                 120                 125

Glu Leu Glu Ser Leu Leu Ser Phe Leu Gln Lys Ser Lys Lys Arg Leu
        130                 135                 140

Thr Asp Ser Glu Phe Lys Asp Pro Glu Thr Gly Lys Thr Cys Leu Leu
145                 150                 155                 160

Lys Ala Met Leu Asn Leu His Asn Gly Gln Asn Asp Thr Ile Ala Leu
                165                 170                 175

Leu Leu Asp Ile Ala Arg Lys Thr Asp Ser Leu Lys Gln Phe Val Asn
                180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
        210                 215                 220

Gly Ala Asp Val Gln Ala Ala Ala Asn Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Ala Ile Val Lys Phe Leu Leu Gln Asn Ser
                260                 265                 270

Trp Gln Pro Ala Asp Ile Ser Ala Arg Asp Ser Val Gly Asn Thr Val
            275                 280                 285

Leu His Ala Leu Val Glu Val Ala Asp Asn Thr Ala Asp Asn Thr Lys
        290                 295                 300

Phe Val Thr Asn Met Tyr Asn Glu Ile Leu Ile Leu Gly Ala Lys Leu
305                 310                 315                 320

His Pro Thr Leu Lys Leu Glu Glu Leu Thr Asn Lys Lys Gly Leu Thr
                325                 330                 335

Pro Leu Ala Leu Ala Ala Ser Ser Gly Lys Ile Gly Val Leu Ala Tyr
                340                 345                 350

Ile Leu Gln Arg Glu Ile His Glu Pro Glu Cys Arg His Leu Ser Arg
            355                 360                 365

Lys Phe Thr Glu Trp Ala Tyr Gly Pro Val His Ser Ser Leu Tyr Asp
        370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
                420                 425                 430

Arg Ile Phe Tyr Phe Asn Phe Val Tyr Cys Leu Tyr Met Ile Ile
            435                 440                 445

Phe Thr Thr Ala Ala Tyr Tyr Arg Pro Val Glu Gly Leu Pro Pro Tyr
        450                 455                 460

Lys Leu Asn Asn Thr Val Gly Asp Tyr Phe Arg Val Thr Gly Glu Ile
465                 470                 475                 480

Leu Ser Val Ser Gly Gly Val Tyr Phe Phe Arg Gly Ile Gln Tyr
                485                 490                 495

Phe Leu Gln Arg Arg Pro Ser Leu Lys Ser Leu Phe Val Asp Ser Tyr
            500                 505                 510

Ser Glu Ile Leu Phe Phe Val Gln Ser Leu Phe Met Leu Val Ser Val
        515                 520                 525

Val Leu Tyr Phe Ser His Arg Lys Glu Tyr Val Ala Ser Met Val Phe
    530                 535                 540

Ser Leu Ala Met Gly Trp Thr Asn Met Leu Tyr Tyr Thr Arg Gly Phe
545                 550                 555                 560

Gln Gln Met Gly Ile Tyr Ala Val Met Ile Glu Lys Met Ile Leu Arg
                565                 570                 575

Asp Leu Cys Arg Phe Met Phe Val Tyr Leu Val Phe Leu Phe Gly Phe
            580                 585                 590

Ser Thr Ala Val Val Thr Leu Ile Glu Asp Gly Lys Asn Asn Ser Leu
        595                 600                 605

Pro Val Glu Ser Pro Pro His Lys Cys Arg Gly Ser Ala Cys Arg Pro
    610                 615                 620

Gly Asn Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
            660                 665                 670

Ile Leu Leu Leu Asn Met Leu Ile Ala Leu Met Gly Glu Thr Val Asn
        675                 680                 685

Lys Ile Ala Gln Glu Ser Lys Asn Ile Trp Lys Leu Gln Arg Ala Ile
    690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Phe Thr Pro Asp Gly Lys
                725                 730                 735

Asp Asp Phe Arg Trp Cys Phe Arg Val Asp Glu Val Asn Trp Thr Thr
            740                 745                 750

Trp Asn Thr Asn Val Gly Ile Ile Asn Glu Asp Pro Gly Asn Cys Glu
        755                 760                 765

Gly Val Lys Arg Thr Leu Ser Phe Ser Leu Arg Ser Gly Arg Val Ser
    770                 775                 780

Gly Arg Asn Trp Lys Asn Phe Ala Leu Val Pro Leu Leu Arg Asp Ala
785                 790                 795                 800

Ser Thr Arg Asp Arg His Ser Thr Gln Pro Glu Glu Val Gln Leu Lys
                805                 810                 815

His Tyr Thr Gly Ser Leu Lys Pro Glu Asp Ala Glu Val Phe Lys Asp
            820                 825                 830

Ser Met Ala Pro Gly Glu Lys
        835

<210> SEQ ID NO 9
<211> LENGTH: 2517
<212> TYPE: DNA
<213> ORGANISM: Artificial Sequence
<220> FEATURE:
<223> OTHER INFORMATION: Human TRPV1

<400> SEQUENCE: 9
atgaagaaat ggagcagcac agacttgggg gcagctgcgg acccactcca aaaggacacc      60
tgcccagacc ccctggatgg agaccctaac tccaggccac ctccagccaa gccccagctc     120

```
tccacggcca agagccgcac ccggctcttt gggaagggtg actcggagga ggctttcccg    180
gtggattgcc ctcacgagga aggtgagctg actcctgcc cgaccatcac agtcagccct    240
gttatcacca tccagaggcc aggagacggc cccaccggtg ccaggctgct gtcccaggac    300
tctgtcgccg ccagcaccga gaagaccctc aggctctatg atcgcaggag tatctttgaa    360
gccgttgctc agaataactg ccaggatctg gagagcctgc tgctcttcct gcagaagagc    420
aagaagcacc tcacagacaa cgagttcaaa gaccctgaga cagggaagac ctgtctgctg    480
aaagccatgc tcaacctgca cgacggacag aacaccacca tcccctgct cctggagatc    540 gcgcggcaaa cggacagcct gaaggagctt gtcaacgcca gctacacgga cagctactac    600
aagggccaga cagcactgca catcgccatc gagagacgca catggccct ggtgaccctc    660 ctggtggaga acgagcagaa cgtccaggct gcggcccatg gggacttctt taagaaaacc    720
aaagggcggc ctggattcta cttcggtgaa ctgcccctgt ccctggccgc gtgcaccaac    780
cagctgggca tcgtgaagtt cctgctgcag aactcctggc agacggccga catcagcgcc    840
agggactcgg tgggcaacac ggtgctgcac gccctggtgg aggtggccga caacacggcc    900
gacaacacga gtttgtgac gagcatgtac aatgagattc tgatgctggg ggccaaactg    960
cacccgacgc tgaagctgga ggagctcacc aacaagaagg gaatgacgcc gctggctctg   1020
gcagctggga ccgggaagat cggggtcttg gcctatattc tccagcggga gatccaggag   1080
cccgagtgca ggcacctgtc caggaagttc accgagtggg cctacgggcc cgtgcactcc   1140
tcgctgtacg acctgtcctg catcgacacc tgcgagaaga actcggtgct ggaggtgatc   1200
gcctacagca gcagcgagac ccctaatcgc cacgacatgc tcttggtgga gccgctgaac   1260
cgactcctgc aggacaagtg ggacagattc gtcaagcgca tcttctactt caacttcctg   1320
gtctactgcc tgtacatgat catcttcacc atggctgcct actacaggcc cgtggatggc   1380
ttgcctccct ttaagatgga aaaaactgga gactatttcc gagttactgg agagatcctg   1440
tctgtgttag gaggagtcta cttcttttc cgagggattc agtatttcct gcagaggcgg   1500
ccgtcgatga agaccctgtt tgtggacagc tacagtgaga tgcttttctt tctgcagtca   1560
ctgttcatgt tggccaccgt ggtgctgtac ttcagccacc tcaaggagta tgtggcttcc   1620
atggtattct ccctggcctt gggctggacc aacatgctct actacacccg cggtttccag   1680
cagatgggca tctatgccgt catgatagag aagatgatcc tgagagacct gtgccgtttc   1740
atgtttgtct acatcgtctt cttgttcggg ttttccacag cggtggtgac gctgattgaa   1800
gacgggaaga atgactccct gccgtctgag tccacgtcgc acaggtggcg ggggcctgcc   1860
tgcaggcccc ccgatagctc ctacaacagc ctgtactcca cctgcctgga gctgttcaag   1920
ttcaccatcg gcatgggcga cctggagttc actgagaact atgacttcaa ggctgtcttc   1980
atcatcctgc tgctggccta tgtaattctc acctacatcc tcctgctcaa catgctcatc   2040
gccctcatgg gtgagactgt caacaagatc gcacaggaga gcaagaacat ctggaagctg   2100
cagagagcca tcaccatcct ggacacggag aagagcttcc ttaagtgcat gaggaaggcc   2160
ttccgctcag gcaagctgct gcaggtgggg tacacacctg atggcaagga cgactaccgg   2220
tggtgcttca gggtggacga ggtgaactgg accacctgga acaccaacgt gggcatcatc   2280
aacgaagacc cggcaactg tgagggcgtc aagcgcaccc tgagcttctc cctgcggtca   2340
agcagagttt caggcagaca ctggaagaac tttgccctgg tccccctttt aagagaggca   2400
agtgctcgag ataggcagtc tgctcagccc gaggaagttt atctgcgaca gttttcaggg   2460
tctctgaagc cagaggacgc tgaggtcttc aagagtcctg ccgcttccgg ggagaag     2517
```

<210> SEQ ID NO 10
<211> LENGTH: 839
<212> TYPE: PRT
<213> ORGANISM: Artificial Sequence
<220> FEATURE:
<223> OTHER INFORMATION: Human TRPV1

<400> SEQUENCE: 10

```
Met Lys Lys Trp Ser Ser Thr Asp Leu Gly Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
        35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110

Tyr Asp Arg Arg Ser Ile Phe Glu Ala Val Ala Gln Asn Asn Cys Gln
        115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
            180                 185                 190

Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
    210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
        355                 360                 365
```

-continued

```
Lys Phe Thr Glu Trp Ala Tyr Gly Pro Val His Ser Ser Leu Tyr Asp
    370                 375                 380
Leu Ser Cys Ile Asp Thr Cys Glu Lys Asn Ser Val Leu Glu Val Ile
385                 390                 395                 400
Ala Tyr Ser Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
            420                 425                 430
Arg Ile Phe Tyr Phe Asn Phe Leu Val Tyr Cys Leu Tyr Met Ile Ile
        435                 440                 445
Phe Thr Met Ala Ala Tyr Tyr Arg Pro Val Asp Gly Leu Pro Pro Phe
    450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Phe Arg Gly Ile Gln Tyr Phe
                485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
        515                 520                 525
Leu Tyr Phe Ser His Leu Lys Glu Tyr Val Ala Ser Met Val Phe Ser
    530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
            580                 585                 590
Thr Ala Val Val Thr Leu Ile Glu Asp Gly Lys Asn Asp Ser Leu Pro
        595                 600                 605
Ser Glu Ser Thr Ser His Arg Trp Arg Gly Pro Ala Cys Arg Pro Pro
    610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
        675                 680                 685
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
    770                 775                 780
```

| | | | | | | | | |
|---|---|---|---|---|---|---|---|---|
|Gly|Arg|His|Trp|Lys|Asn|Phe|Ala|Leu|Val|Pro|Leu|Leu|Arg|Glu|Ala|
|785| | | | |790| | | | |795| | | | |800|

Ser Ala Arg Asp Arg Gln Ser Ala Gln Pro Glu Glu Val Tyr Leu Arg
            805                 810                 815

Gln Phe Ser Gly Ser Leu Lys Pro Glu Asp Ala Glu Val Phe Lys Ser
            820                 825                 830

Pro Ala Ala Ser Gly Glu Lys
        835

<210> SEQ ID NO 11
<211> LENGTH: 2868
<212> TYPE: DNA
<213> ORGANISM: Artificial Sequence
<220> FEATURE:
<223> OTHER INFORMATION: ANO1 mouse

<400> SEQUENCE: 11

| | | |
|---|---|---|
|atgagggtcc ccgagaagta ctcgacgctc ccggcggagg accgcagcgt ccacatcgtg|60|
|aacatctgcg ccatcgagga cctgggctac ctgccgtccg agggcacgtt gctgaactct|120|
|ctgtccgtgg accccgacgc cgaatgcaag tatggactat acttcaggga tggcaaacgg|180|
|aaggtggact acatcttggt ataccatcac aagagagcct cagggagcag gactctggcc|240|
|aggaggggac tacaaaatga catggtcctg ggacccgca gcgtcaggca ggaccagccc|300|
|cttcccggga aggggagccc tgtggatgca ggctcaccgg aagtccccat ggattaccat|360|
|gaagatgaca aacgcttcag acgggaggaa tatgagggca acctgttgga ggcaggcctg|420|
|gagttggaga atgacgagga taccaaaatc catggtgtcg ggtttgtgaa gatccatgcg|480|
|ccctggcatg tgctctgtag ggaagctgag tttttgaaac taaagatgcc cacaaagaag|540|
|gtgtaccaca tcagtgagac gcgaggcctc ctgaaaacca tcaactcggt tctgcagaag|600|
|atcacagacc ccatccagcc caaggtggct gagcacaggc cacagaccac aaagaggctc|660|
|tcctatccct ctcccgggga agcaacac ctattcgacc tgactgacag ggactctttt|720|
|ttcgacagca aaacccggag cacaatagtc tatgaaatcc tgaagagaac aacgtgcacc|780|
|aaggccaagt acagcatggg tatcaccagc ctcctggcca atggcgtata ctcagctgca|840|
|taccctctgc acgatgggga ctatgagggt gacaacgttg agttcaacga caggaaactc|900|
|ctgtatgagg aatgggcaag ttacggagtc ttctacaaat accagcccat tgacctggtc|960|
|aggaaatact ttggtgagaa ggttggcctg tactttgcct ggcttggagc ctacacccag|1020|
|atgctcatcc ctgcctcgat cgtgggtgtc attgtctttc tctatggatg tgccactgtg|1080|
|gacgaaaaca tccccagtat ggagatgtgt gaccagagat acaacatcac catgtgtcct|1140|
|ctgtgtgaca gacctgcag ctactggaag atgagctcag cctgtgccac agcccgtgcc|1200|
|agtcaccttt ttgataaccc tgccaccgtc ttcttctctg tgtttatggc cctctgggct|1260|
|gccactttca tggagcactg gaaacggaag cagatgaggc tcaactaccg atgggaccto|1320|
|acaggcttcg aggaggagga ggatcatccc agagcagagt atgaagccag agtcttagag|1380|
|aagtcactga aaaagaatc cagaaacaaa gagaccgaca aggtgaagct gacctggagg|1440|
|gaccgattcc cagcctattt caccaatctt gtctccatca tcttcatgat cgcagtgaca|1500|
|tttgcaatcg tcctcggagt tatcatctat agaatctcca cagctgcagc cttggccatg|1560|
|aactcctccc cgtctgtgcg gtccaacatc cgggttacag tcacggccac cgctgttatc|1620|
|atcaacctcg tggtcatcat tctgctggat gaagtttacg gctgcattgc caggtggctc|1680|
|accaagattg aggtcccaaa gacagagaag agctttgagg agaggctaac cttcaaggcc|1740|

```
ttcctgctca agtttgtgaa ctcttacact cccatcttct atgtcgcctt cttcaaaggc    1800
cggtttgttg gtcggcccgg tgactacgtg tacatcttcc gctctttccg gatggaggag    1860
tgtgccccgg gcggctgcct catggagctc tgtatccagc tgagcatcat tatgctgggc    1920
aagcagctaa tccagaacaa tctcttcgag attggcatcc cgaagatgaa aaagttcatc    1980
cgctacctga agctgcgcag acagagcccc tcagaccgtg aagagtacgt gaagcggaag    2040
cagcgctatg aggtggactt caacctcgaa cctttcgccg gcctcacgcc cgagtacatg    2100
gaaatgatca ttcagttcgg ctttgtcacc ctgtttgttg cgtccttccc tctggctcca    2160
ctcttcgccc tgctaaacaa catcattgag atccgcctgg atgccaaaaa gtttgtcacc    2220
gagctacgga ggccagtagc catcagagcc aaagacatcg catctggta taacatcctc    2280
agaggtgttg ggaagctggc tgtcatcatt aatgcctttg tgatctcctt cacgtctgac    2340
ttcatccctc gcctggtgta cctctacatg tacagtcaga atgggaccat gcacggcttc    2400
gtcaatcaca cgctctcttc cttcaatgtc agcgacttcc agaatggcac agcacccaat    2460
gacccactgg acctgggcta tgaggttcag atctgcaggt ataaagatta ccgggaaccc    2520
ccatggtcag aacacaagta tgacatctcc aaagacttct gggctgtcct ggccgcccga    2580
ctggcatttg tcattgtctt ccagaacctg gtgatgttca tgagtgactt tgtggactgg    2640
gtgatccctg atatccccaa agacatcagc cagcagatcc acaaagagaa ggttctcatg    2700
gtggagctgt ttatgcgtga ggagcagggc aagcagcagc tactgacac atggatggag    2760
aaggagaagc caagggatgt gccttgtaac aaccacagcc ccacaaccca cccagaggca    2820
ggcgacggca gcccagtccc cagctacgag taccatgggg acgcgctg               2868
```

<210> SEQ ID NO 12
<211> LENGTH: 956
<212> TYPE: PRT
<213> ORGANISM: Artificial Sequence
<220> FEATURE:
<223> OTHER INFORMATION: ANO1 mouse

<400> SEQUENCE: 12

```
Met Arg Val Pro Glu Lys Tyr Ser Thr Leu Pro Ala Glu Asp Arg Ser
1               5                   10                  15

Val His Ile Val Asn Ile Cys Ala Ile Glu Asp Leu Gly Tyr Leu Pro
            20                  25                  30

Ser Glu Gly Thr Leu Leu Asn Ser Leu Ser Val Asp Pro Asp Ala Glu
        35                  40                  45

Cys Lys Tyr Gly Leu Tyr Phe Arg Asp Gly Lys Arg Lys Val Asp Tyr
    50                  55                  60

Ile Leu Val Tyr His His Lys Arg Ala Ser Gly Ser Arg Thr Leu Ala
65                  70                  75                  80

Arg Arg Gly Leu Gln Asn Asp Met Val Leu Gly Thr Arg Ser Val Arg
                85                  90                  95

Gln Asp Gln Pro Leu Pro Gly Lys Gly Ser Pro Val Asp Ala Gly Ser
            100                 105                 110

Pro Glu Val Pro Met Asp Tyr His Glu Asp Lys Arg Phe Arg Arg
        115                 120                 125

Glu Glu Tyr Glu Gly Asn Leu Leu Glu Ala Gly Leu Glu Leu Glu Asn
    130                 135                 140

Asp Glu Asp Thr Lys Ile His Gly Val Gly Phe Val Lys Ile His Ala
145                 150                 155                 160
```

```
Pro Trp His Val Leu Cys Arg Glu Ala Glu Phe Leu Lys Leu Lys Met
            165                 170                 175

Pro Thr Lys Lys Val Tyr His Ile Ser Glu Thr Arg Gly Leu Leu Lys
        180                 185                 190

Thr Ile Asn Ser Val Leu Gln Lys Ile Thr Asp Pro Ile Gln Pro Lys
    195                 200                 205

Val Ala Glu His Arg Pro Gln Thr Thr Lys Arg Leu Ser Tyr Pro Phe
210                 215                 220

Ser Arg Glu Lys Gln His Leu Phe Asp Leu Thr Asp Arg Asp Ser Phe
225                 230                 235                 240

Phe Asp Ser Lys Thr Arg Ser Thr Ile Val Tyr Glu Ile Leu Lys Arg
                245                 250                 255

Thr Thr Cys Thr Lys Ala Lys Tyr Ser Met Gly Ile Thr Ser Leu Leu
            260                 265                 270

Ala Asn Gly Val Tyr Ser Ala Ala Tyr Pro Leu His Asp Gly Asp Tyr
        275                 280                 285

Glu Gly Asp Asn Val Glu Phe Asn Asp Arg Lys Leu Leu Tyr Glu Glu
    290                 295                 300

Trp Ala Ser Tyr Gly Val Phe Tyr Lys Tyr Gln Pro Ile Asp Leu Val
305                 310                 315                 320

Arg Lys Tyr Phe Gly Glu Lys Val Gly Leu Tyr Phe Ala Trp Leu Gly
                325                 330                 335

Ala Tyr Thr Gln Met Leu Ile Pro Ala Ser Ile Val Gly Val Ile Val
            340                 345                 350

Phe Leu Tyr Gly Cys Ala Thr Val Asp Glu Asn Ile Pro Ser Met Glu
        355                 360                 365

Met Cys Asp Gln Arg Tyr Asn Ile Thr Met Cys Pro Leu Cys Asp Lys
    370                 375                 380

Thr Cys Ser Tyr Trp Lys Met Ser Ser Ala Cys Ala Thr Ala Arg Ala
385                 390                 395                 400

Ser His Leu Phe Asp Asn Pro Ala Thr Val Phe Phe Ser Val Phe Met
                405                 410                 415

Ala Leu Trp Ala Ala Thr Phe Met Glu His Trp Lys Arg Lys Gln Met
            420                 425                 430

Arg Leu Asn Tyr Arg Trp Asp Leu Thr Gly Phe Glu Glu Glu Glu Asp
        435                 440                 445

His Pro Arg Ala Glu Tyr Glu Ala Arg Val Leu Glu Lys Ser Leu Arg
    450                 455                 460

Lys Glu Ser Arg Asn Lys Glu Thr Asp Lys Val Lys Leu Thr Trp Arg
465                 470                 475                 480

Asp Arg Phe Pro Ala Tyr Phe Thr Asn Leu Val Ser Ile Ile Phe Met
                485                 490                 495

Ile Ala Val Thr Phe Ala Ile Val Leu Gly Val Ile Ile Tyr Arg Ile
            500                 505                 510

Ser Thr Ala Ala Ala Leu Ala Met Asn Ser Ser Pro Ser Val Arg Ser
        515                 520                 525

Asn Ile Arg Val Thr Val Thr Ala Thr Ala Val Ile Ile Asn Leu Val
    530                 535                 540

Val Ile Ile Leu Leu Asp Glu Val Tyr Gly Cys Ile Ala Arg Trp Leu
545                 550                 555                 560

Thr Lys Ile Glu Val Pro Lys Thr Glu Lys Ser Phe Glu Glu Arg Leu
                565                 570                 575
```

```
Thr Phe Lys Ala Phe Leu Leu Lys Phe Val Asn Ser Tyr Thr Pro Ile
            580                 585                 590

Phe Tyr Val Ala Phe Phe Lys Gly Arg Phe Val Gly Arg Pro Gly Asp
        595                 600                 605

Tyr Val Tyr Ile Phe Arg Ser Phe Arg Met Glu Glu Cys Ala Pro Gly
    610                 615                 620

Gly Cys Leu Met Glu Leu Cys Ile Gln Leu Ser Ile Ile Met Leu Gly
625                 630                 635                 640

Lys Gln Leu Ile Gln Asn Asn Leu Phe Glu Ile Gly Ile Pro Lys Met
                645                 650                 655

Lys Lys Phe Ile Arg Tyr Leu Lys Leu Arg Arg Gln Ser Pro Ser Asp
            660                 665                 670

Arg Glu Glu Tyr Val Lys Arg Lys Gln Arg Tyr Glu Val Asp Phe Asn
        675                 680                 685

Leu Glu Pro Phe Ala Gly Leu Thr Pro Glu Tyr Met Glu Met Ile Ile
    690                 695                 700

Gln Phe Gly Phe Val Thr Leu Phe Val Ala Ser Phe Pro Leu Ala Pro
705                 710                 715                 720

Leu Phe Ala Leu Leu Asn Asn Ile Ile Glu Ile Arg Leu Asp Ala Lys
                725                 730                 735

Lys Phe Val Thr Glu Leu Arg Arg Pro Val Ala Ile Arg Ala Lys Asp
            740                 745                 750

Ile Gly Ile Trp Tyr Asn Ile Leu Arg Gly Val Gly Lys Leu Ala Val
        755                 760                 765

Ile Ile Asn Ala Phe Val Ile Ser Phe Thr Ser Asp Phe Ile Pro Arg
    770                 775                 780

Leu Val Tyr Leu Tyr Met Tyr Ser Gln Asn Gly Thr Met His Gly Phe
785                 790                 795                 800

Val Asn His Thr Leu Ser Ser Phe Asn Val Ser Asp Phe Gln Asn Gly
                805                 810                 815

Thr Ala Pro Asn Asp Pro Leu Asp Leu Gly Tyr Glu Val Gln Ile Cys
            820                 825                 830

Arg Tyr Lys Asp Tyr Arg Glu Pro Pro Trp Ser Glu His Lys Tyr Asp
        835                 840                 845

Ile Ser Lys Asp Phe Trp Ala Val Leu Ala Ala Arg Leu Ala Phe Val
    850                 855                 860

Ile Val Phe Gln Asn Leu Val Met Phe Met Ser Asp Phe Val Asp Trp
865                 870                 875                 880

Val Ile Pro Asp Ile Pro Lys Asp Ile Ser Gln Gln Ile His Lys Glu
                885                 890                 895

Lys Val Leu Met Val Glu Leu Phe Met Arg Glu Glu Gln Gly Lys Gln
            900                 905                 910

Gln Leu Leu Asp Thr Trp Met Glu Lys Glu Lys Pro Arg Asp Val Pro
        915                 920                 925

Cys Asn Asn His Ser Pro Thr Thr His Pro Glu Ala Gly Asp Gly Ser
    930                 935                 940

Pro Val Pro Ser Tyr Glu Tyr His Gly Asp Ala Leu
945                 950                 955

<210> SEQ ID NO 13
<211> LENGTH: 378
<212> TYPE: DNA
<213> ORGANISM: Artificial Sequence
<220> FEATURE:
<223> OTHER INFORMATION: Human D5
```

<400> SEQUENCE: 13

```
gtaagtccac cccacacttc catggcacct gcacaagatg aagagcggga ttcaggaaaa      60
gaacaagggc atactcgtag acatgactgg ggccatgaaa acaaagaaa acataatctt     120
ggccatggcc ataaacatga acgtgaccaa gggcatgggc accaaagagg acatggcctt    180
ggccatggac acgaacaaca gcatggtctt ggtcatggac ataagttcaa acttgatgat    240
gatcttgaac accaagggg ccatgtcctt gaccatggac ataagcataa gcatggtcat     300
ggccacggaa acataaaaa taaggcaaa aagaatggaa agcacaatgg ttggaaaaca      360
gagcatttgg caagcttg                                                   378
```

<210> SEQ ID NO 14
<211> LENGTH: 126
<212> TYPE: PRT
<213> ORGANISM: Artificial Sequence
<220> FEATURE:
<223> OTHER INFORMATION: Human D5

<400> SEQUENCE: 14

```
Val Ser Pro Pro His Thr Ser Met Ala Pro Ala Gln Asp Glu Glu Arg
1               5                   10                  15

Asp Ser Gly Lys Glu Gln Gly His Thr Arg Arg His Asp Trp Gly His
            20                  25                  30

Glu Lys Gln Arg Lys His Asn Leu Gly His Gly His Lys His Glu Arg
        35                  40                  45

Asp Gln Gly His Gly His Gln Arg Gly His Gly Leu Gly His Gly His
    50                  55                  60

Glu Gln Gln His Gly Leu Gly His Gly His Lys Phe Lys Leu Asp Asp
65                  70                  75                  80

Asp Leu Glu His Gln Gly Gly His Val Leu Asp His Gly His Lys His
                85                  90                  95

Lys His Gly His Gly His Gly Lys His Lys Asn Lys Gly Lys Lys Asn
            100                 105                 110

Gly Lys His Asn Gly Trp Lys Thr Glu His Leu Ala Ser Leu
        115                 120                 125
```

<210> SEQ ID NO 15
<211> LENGTH: 34
<212> TYPE: PRT
<213> ORGANISM: Artificial Sequence
<220> FEATURE:
<223> OTHER INFORMATION: Human D5a

<400> SEQUENCE: 15

```
Gly His Gly Leu Gly His Gly His Glu Gln Gln His Gly Leu Gly His
1               5                   10                  15

Gly His Lys Phe Lys Leu Asp Asp Leu Glu His Gln Gly Gly His
            20                  25                  30

Val Leu
```

<210> SEQ ID NO 16
<211> LENGTH: 29
<212> TYPE: PRT
<213> ORGANISM: Artificial Sequence
<220> FEATURE:
<223> OTHER INFORMATION: Human D5b

```
-continued

<400> SEQUENCE: 16

Asp His Gly His Lys His Lys His Gly His Gly His Gly Lys His Lys
1               5                   10                  15

Asn Lys Gly Lys Lys Asn Gly Lys His Asn Gly Trp Lys
            20                  25

<210> SEQ ID NO 17
<211> LENGTH: 14
<212> TYPE: PRT
<213> ORGANISM: Artificial Sequence
<220> FEATURE:
<223> OTHER INFORMATION: Human D5c

<400> SEQUENCE: 17

Asp His Gly His Lys His Lys His Gly His Gly His Gly Lys
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Human D5d

<400> SEQUENCE: 18

His Gly His Gly His Gly Lys His Lys Asn Lys Gly Lys Lys Asn Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Human D5e

<400> SEQUENCE: 19

His Lys Asn Lys Gly Lys Lys Asn Gly Lys His Asn Gly Trp Lys
1               5                   10                  15

<210> SEQ ID NO 20
<211> LENGTH: 22
<212> TYPE: PRT
<213> ORGANISM: Artificial Sequence
<220> FEATURE:
<223> OTHER INFORMATION: Human D5f

<400> SEQUENCE: 20

His Gly His Gly His Gly Lys His Lys Asn Lys Gly Lys Lys Asn Gly
1               5                   10                  15

Lys His Asn Gly Trp Lys
            20
```

POLYPEPTIDES, RELATED NUCLEIC ACIDS, AND THEIR USES FOR CELL MODULATION AND TREATMENTS

CROSS-REFERENCE TO RELATED APPLICATIONS

This application is a National Stage Entry of International Application No. PCT/US2015/038948 filed Jul. 2, 2015, which is herein incorporated by reference in its entirety, which claims the benefit of U.S. Provisional Application No. 62/020,470, filed Jul. 3, 2014, entitled "Systems and Methods For Controlling Cells and Biological Systems Remotely" which is herein incorporated by reference in its entirety.

BACKGROUND

Thermal sensitive ion channels have been studied for several years. In certain instances, heat can alter ion flow or membrane potential in membranes that comprise thermal sensitive ion channels. This alteration can, under some circumstances, provide a change in the intracellular environment; if that cell is in an animal (e.g., human) then the alteration can sometimes provide a change in the animal physiology.

Ferritin is a ubiquitous intracellular protein that stores iron and has been studied for several years. Ferritin is produced by many animals (e.g., humans) and can be found in many biological tissues as a cytosolic protein (e.g., in the cytosol of a cell). In some circumstances, ferritin can be heated by radiofrequency fields.

SUMMARY

Certain embodiments of the invention include polypeptides that comprise (a) a thermal sensitive ion channel or a variant thereof linked to (b) a domain 5 of kininogen 1 or a variant or fragment thereof. Other embodiments include nucleic acid molecules that encode the polypeptide. In additional embodiments, compositions can comprise the polypeptide or compositions can comprise the nucleic acid molecule. In further embodiments, pharmaceutical compositions can comprise the polypeptide or compositions can comprise the nucleic acid molecule.

Other embodiments of the invention include methods for modulating a cell comprising administering a composition comprising a nucleic acid molecule to at least one cell and applying a static magnetic field or an electromagnetic field, where the cell is modulated upon applying the static magnetic field or the electromagnetic field. Yet other embodiments include methods for modulating at least one cell in an animal (e.g., human) comprising administering a composition comprising a nucleic acid molecule to the animal (e.g., human) and applying a static magnetic field or an electromagnetic field, where the at least one cell is modulated upon applying the static magnetic field or the electromagnetic field.

Some embodiments of the invention include methods for treating an animal (e.g., human) for a disease or disorder, comprising administering a composition comprising a nucleic acid molecule to the animal and applying a static magnetic field or an electromagnetic field, where at least one cell in the animal (e.g., human) is modulated upon applying the static magnetic field or the electromagnetic field, and the modulation treats the disease or disorder.

BRIEF DESCRIPTION OF THE DRAWINGS

The following drawings form part of the present specification and are included to further demonstrate certain embodiments of the present invention. The invention may be better understood by reference to one or more of these drawings in combination with the description of specific embodiments presented herein.

FIG. 7 provides illustrations of some embodiments of the inventive polypeptide and its modulation of the cell membrane upon application of RF.

FIG. 8 is a TRPV1.D5 fusion gene cloned into pLVX. Expression is driven by the EF1a promoter. There is an IRES site downstream of TRPV1.D5 to drive expression of mCherry.

FIG. 9 shows ferritin distribution to membranes in HEK293 cells and demonstrates interaction of ferritin with TRPV1.D5 but not TRPV1. Confocal images of ferritin (white) in TRPV1 (FIG. 9a) and TRPV1.D5 (FIG. 9b) cells. TEM images of membranes in TRPV1 (FIG. 9c) and TRPV1.D5 (FIG. 9d) cells. The bar under FIG. 9d is the scale for FIG. 9c and FIG. 9d and represents a length of 0.1 microns.

FIG. 14a is the control (no RF applied). FIG. 14b and FIG. 14c show the increased immunoreactivity with anti phospho-specific CaMKii antibody after stimulation with RF.

FIG. 15 shows RF activated TRPV1.D5 in the cardiac neural crest cells results in heart defects which can be rescued by pretreatment with a TRPV1 inhibitor. Normal outflow vessel alignment with the base aorta (Ao) wedged behind the pulmonary trunk (Pa) (FIG. 15a) from a chick embryo not activated with RF. Rightward displaced aorta (Ao) positioned over the right ventricle (DORV) in an embryo exposed to RF for 10 minutes in (FIG. 15b—arrowheads). FIG. 15c and FIG. 15d show H&E stained cross section of hearts in FIG. 15a and FIG. 15b showing the associated ventricular septal defect (VSD) (arrow in FIG. 15d) in the DORV heart.

DETAILED DESCRIPTION

Figure 7A:
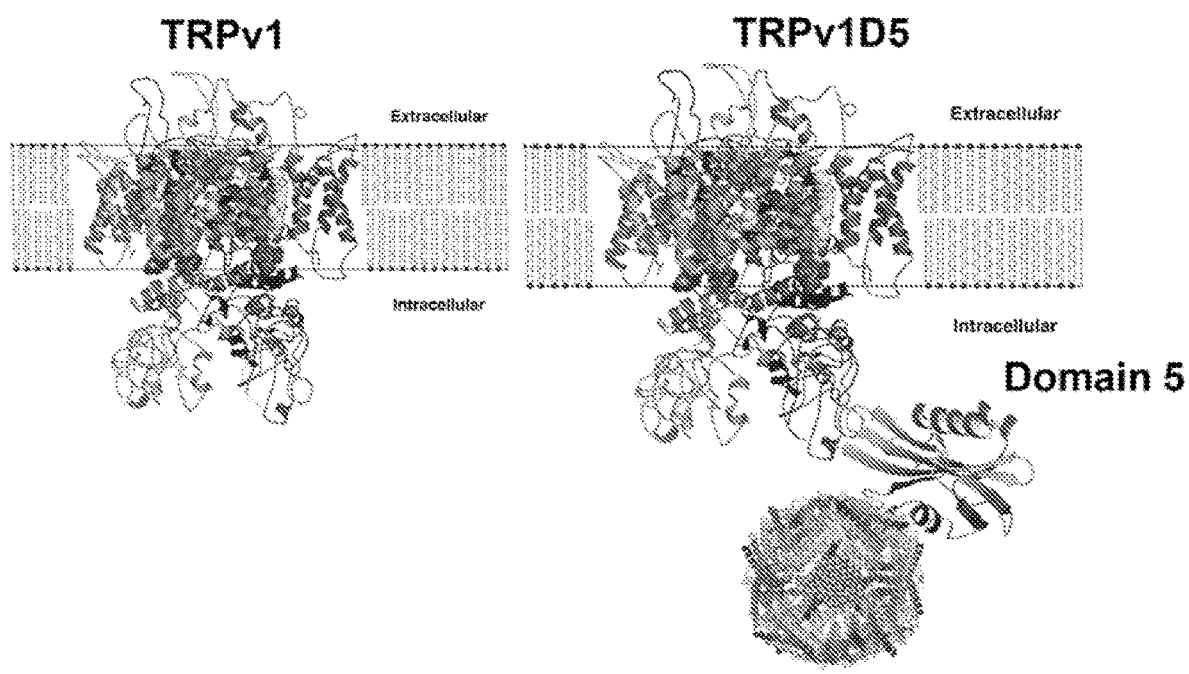
FIG. 7a is an illustration of recruitment of ferritin to TRPV1 channel through domain 5 that is expressed at the c-terminal of the channel.
Figure 7B:
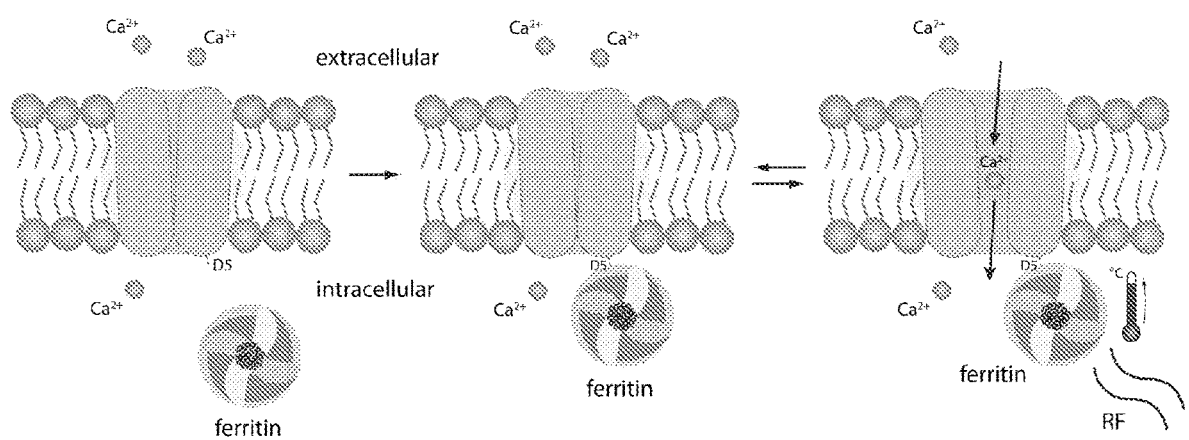
FIG. 7b shows a cartoon representation of an exemplary embodiment of the inventive polypeptide. The left and center pictures show that the inventive polypeptide (via D5) interacts with endogenous ferritin. The right picture provides an embodiment such that application of RF, which provides heat, can modulate ion flow (e.g., $Ca^{2+}$).

Disclosed herein are inventive polypeptides (e.g., comprising a thermal sensitive ion channel or variant thereof and a domain 5 of kininogen 1 or variant or fragment thereof) and nucleic acid molecules encoding inventive polypeptides. Also disclosed are methods for modulating a cell comprising administering certain compositions (e.g., pharmaceutical compositions of the nucleic acid molecule) and applying static magnetic field(s) or electromagnetic field(s). Methods for treating diseases or disorders in an animal (e.g., human) comprising administering certain compositions (e.g., pharmaceutical compositions of the nucleic acid molecule) and applying a static magnetic field or an electromagnetic field, are further disclosed. Some embodiments of the invention are illustrated in FIG. 7.

In certain embodiments, administration of a nucleic acid molecule results in expression of the encoded inventive polypeptide. In other embodiments, the thermal sensitive ion channel or variant thereof portion of the inventive polypeptide resides in the membrane of a cell and the domain 5 of kininogen 1 or variant or fragment thereof portion of the inventive polypeptide resides in a cell space or compartment that comprises ferritin (e.g., the cytosol). In certain embodiments, and without being bound by theory, ferritin (e.g., endogenous ferritin) is in close proximity to the inventive polypeptide (e.g., because, in some embodiments, ferritin binds to or is associated with the domain 5 of kininogen 1 or variant or fragment thereof portion of the inventive polypeptide). Without being bound by theory, the close proximity of ferritin can sometimes permit the application of heat (e.g., by application of an electromagnetic field) or mechanical force (e.g., by the application of a static magnetic field) to the inventive polypeptide (and by implication the membrane of cell in which the inventive polypeptide resides) via the iron in ferritin. Thus, in some embodiments and without being bound by theory, the close proximity of ferritin to the inventive polypeptide permits modulation of certain aspects of the cell membrane and/or cell.

Inventive Polypeptides, Nucleic Acid Molecules, and Compositions

Some embodiments of the inventive polypeptides comprise (a) a thermal sensitive ion channel or a variant thereof and (b) domain 5 of kininogen 1 or a variant or fragment thereof.

Any suitable thermal sensitive ion channel can form the basis of the thermal sensitive ion channel or a variant thereof of the inventive polypeptide. In certain embodiments, thermal sensitive ion channels encompass any ion channel that can be modulated by temperature. "Modulate" (or any variation thereof) as generally used herein is defined as change, such as, but limited to an increase or a decrease, or change of state (e.g., conformational change in a protein). "Modulation of a cell" (or any variation thereof), as used herein, is defined as any change in a cell, such as, but not limited to, an increase, a decrease, a reversal, a starting or a stopping of the flow of one or more ions and/or a change of state (e.g., polarization of a membrane, repolarization of a membrane, depolarization of a membrane or hyperpolarization of a membrane) that can influence of one or more molecules or one or more cell systems. For example, modulation of the thermal sensitive ion channel can modulate the membrane potential, the ion flow, or both. Modulation of the membrane potential can, in some instances, result in polarization, repolarization, depolarization, or hyperpolarization (e.g., in a neuron, a glial cell, a cancer cell, an airway epithelial cell, or an immune cell). For example, modulation of the inventive polypeptide (e.g., the thermal sensitive ion channel portion of the inventive polypeptide) can open, partially open, close, partially close or reverse ion flow in the ion channel when the temperature is increased or when the temperature is decreased. The inventive polypeptide (e.g., the thermal sensitive ion channel portion of the inventive polypeptide) can include, but is not limited to, ion channels that can modulate the flow of $Ca^{2+}$, $Mg^{2+}$, $Ba^{2+}$, $Be^{2+}$, $I^-$, $Br^-$, $Cl^-$, $F^-$, $Tl^+$, $Cs^+$, $Rb^+$, $K^+$, $Na^+$, $Li^+$, $H^+$, or combinations thereof. In some embodiments, the inventive polypeptide (e.g., the thermal sensitive ion channel portion of the inventive polypeptide) can include, but is not limited to, ion channels that can modulate the flow of $Ca^{2+}$, $Mg^{2+}$, $I^-$, $Cl^-$, $Tl^+$, $K^+$, $Na^+$, or combinations thereof. In other embodiments, the inventive polypeptide (e.g., the thermal sensitive ion channel portion of the inventive polypeptide) can modulate the flow of one or more ions (e.g., it can modulate two ions, such as both $K^+$ and $Tl^+$). Modulation of ion flow by an inventive polypeptide (e.g., the thermal sensitive ion channel portion of the inventive polypeptide) can include, but is not limited to increasing ion flow, decreasing ion flow, starting ion flow, stopping ion flow, or reversing the direction of ion flow.

In some embodiments, the thermal sensitive ion channel can encompass any known wild type thermal sensitive ion channel (i.e., as found in nature). In other embodiments, the thermal sensitive ion channel is natively found in an animal, such as but not limited to mammals, primates, monkeys (e.g., macaque, rhesus macaque, or pig tail macaque), humans, canine, feline, bovine, porcine, avian (e.g., chicken), mice, rabbits, and rats. In certain embodiments, thermal sensitive ion channel can be any thermal sensitive channel from the transient receptor potential channel (such as any thermal sensitive ion channel from the subfamilies of TRPC, TRPV, TRPA, TRPM, TRPP, TRPML, or TRPN). In some embodiments, the thermal sensitive channel can be TRPV1 (transient receptor potential cation channel subfamily V member 1), TRPV4 (transient receptor potential cation channel subfamily V member 4), ANO1 (Anoctamin-1 also known as Transmembrane member 16A), or TREK-1 (also known as Potassium channel subfamily K member 2). In some embodiments, variants of the thermal sensitive ion channel can include one or more conservative mutations as defined herein, and can encompass known, functionally competent thermal sensitive ion channels (e.g., SEQ ID NO:8, SEQ ID NO:10, or SEQ ID NO:12). In some embodiments, variants of thermal sensitive ion channel can include amino acid sequences that have at least about 80%, at least about 85%, at least about 90%, or at least about 95% sequence identity to the thermal sensitive ion channel. Examples of such sequence identity include about 80, about 81, about 82, about 83, about 84, about 85, about 86, about 87, about 88, about 89, about 90, about 91, about 92, about 93, about 94, about 95, about 96, about 97, about 98, about 99, and about 100%.

Any suitable domain 5 of kininogen 1 can form the basis of the domain 5 of kininogen 1 or fragment or variant thereof. In some embodiments, the domain 5 of kininogen 1 is natively found in an animal, such as but not limited to mammals, primates, monkeys (e.g., macaque, rhesus macaque, or pig tail macaque), humans, canine, feline, bovine, porcine, avian (e.g., chicken), mice, rabbits, and rats. In certain embodiments, domain 5 of kininogen 1 encompasses any known wild type domain 5 of kininogen 1 (i.e., as found in nature), such as V384-K502 (with amino acid numbering defined with respect to the full kininogen 1 protein—See, for example Coffman et al., PNAS (2009) Vol. 106, No. 2, pp. 570-575). In some embodiments, domain 5 of kininogen, its fragments, or its variants encompass such amino acid sequences which have some capacity to bind ferritin (e.g., endogenous ferritin, mammalian ferritin, primate ferritin, murine ferritin, or human ferritin), such as mammalian domain 5 of kininogen 1 including but not limited to human domain 5 of kininogen 1 (SEQ ID NO: 14). In some embodiments, fragments of domain 5 of kininogen 1 can include at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, or at least about 120 consecutive amino acids from a wild type domain 5 of kininogen 1 (e.g., the wild type domain 5 of kininogen 1 can be SEQ ID NO:14). In some embodiments, fragments of domain 5 of kininogen 1 can include about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 55, about 60, about 65, about 70, about 75, about 80, about 90, about 100, about 110, or about 120 consecutive amino acids from a wild type domain 5 of kininogen 1 (e.g., the wild type domain 5 of kininogen 1 can be SEQ ID NO:14). In some embodiments, fragments of domain 5 of kininogen 1 include human portions of domain 5 kininogen 1 such as the following peptide segments (with amino acid numbering defined with respect to the full kininogen 1 protein—See, for example Coffman et al., PNAS (2009) Vol. 106, No. 2, pp. 570-575): G440-L473 (SEQ ID NO: 15); D474-K502 (SEQ ID NO: 16); D474-K487 (SEQ ID NO: 17); H481-G496 (SEQ ID NO: 18); H488-K502 (SEQ ID NO: 19); and H481-K502 (SEQ ID NO: 20). In some embodiments, the fragment of domain 5 of kininogen 1 is not D474-K487. In some embodiments, fragments of domain 5 of kininogen 1 include portions of domain 5 kininogen 1 that are rich in one or more (e.g., 1, 2 or all three) of histidine, glycine, or lysine. In some embodiments, mutations, truncations, additions, deletions, substitutions (e.g., conservative substitutions), or other alterations of the sequence are included in the definition of fragment, provided some degree of ferritin binding is preserved. In other embodiments, variants of domain 5 of kininogen 1 can include one or more mutations, truncations, deletions, additions, or substitutions (e.g., conservative substitutions) from a wild type domain 5 of kininogen 1 (e.g., a wild type domain 5 of kininogen 1 can be SEQ ID NO:14). Variants of domain 5 of kininogen 1 include amino acid sequences that have at least about 80%, at least about 85%, at least about 90%, or at least about 95% sequence identity to the domain 5 of kininogen 1. Examples of such sequence identity include about 80, about 81, about 82, about 83, about 84, about 85, about 86, about 87, about 88, about 89, about 90, about 91, about 92, about 93, about 94, about 95, about 96, about 97, about 98, about 99, and about 100%.

In some embodiments, the inventive polypeptide is a fusion protein that uses a linker to connect the thermal sensitive ion channel or variant thereof to the domain 5 of kininogen 1 or a variant or fragment thereof. In certain embodiments, the linker can be a covalent bond or is no more than 50 amino acids. In some embodiments, the linker is about 1, about 2, about 3, about 4, about 5, about 6, about 7, about 8, about 9, about 10, about 11, about 12, about 13, about 14, about 15, about 16, about 17, about 18, about 19, about 20, no more than 20, no more than 10, from about 1 to about 50, from about 1 to about 20, from about 1 to about 10, from about 1 to about 6, from about 2 to about 6, from about 2 to about 5, or from about 3 to about 4 amino acids. In some embodiments, the linker comprises AAAT, SR, CSR, or WSR (i.e., in single letter amino acid notation). The linker can be any suitable linker and occur at the n-terminus, c-terminus, or anywhere within the sequence (which could require two linkers) of the thermal sensitive ion channel or variant thereof, so long as the domain 5 of kininogen 1 or variant or fragment thereof is in a place (e.g., compartment) in the cell or organelle that comprises ferritin (e.g., the cytoplasm, cytosol, or endoplasmic reticulum).

Some embodiments of the inventive polypeptide include, but are not limited to mouse TRPV1 linked to human domain 5 of kininogen 1 (SEQ ID NO:2) (also referred to herein as TRPV1.D5 or TRPv1.D5), human TRPV1 linked to human domain 5 of kininogen 1 (SEQ ID NO: 4), TRPV1 (e.g., from human, murine, or a mammal) fused to a domain 5 of kininogen 1 or variant or fragment thereof (e.g., from human, murine, or a mammal), TRPV1 variant (e.g., from human, murine, or a mammal) fused to a domain 5 of kininogen 1 or variant or fragment thereof (e.g., from human, murine, or a mammal), TRPV4 (e.g., from human, murine, or a mammal) fused to domain 5 of kininogen 1 or variant or fragment thereof (e.g., from human, murine, or a mammal), TRPV4 variant (e.g., from human, murine, or a mammal) fused to domain 5 of kininogen 1 or variant or fragment thereof (e.g., from human, murine, or a mammal), ANO1 (e.g., from human, murine, or a mammal) fused to domain 5 of kininogen 1 or variant or fragment thereof (e.g., from human, murine, or a mammal), ANO1 variant (e.g., from human, murine, or a mammal) fused to domain 5 of kininogen 1 or variant or fragment thereof (e.g., from human, murine, or a mammal), TREK1 (e.g., from human, murine, or a mammal) fused to a domain 5 of kininogen 1 or variant or fragment thereof variant (e.g., from human, murine, or a mammal), or TREK1 (e.g., from human, murine, or a mammal) fused to a domain 5 of kininogen 1 or variant or fragment thereof (e.g., from human, murine, or a mammal). In some instances, the animal origin of the thermal sensitive ion channel or variant thereof is different from the animal origin of the domain 5 of kininogen 1 or a variant or fragment thereof. In other instances, the animal origin of the thermal sensitive ion channel or variant thereof is the same as the animal origin of the domain 5 of kininogen 1 or a variant or fragment thereof.

Some embodiments of the inventive polypeptide include variants of SEQ ID NO: 2, SEQ ID NO:4, or SEQ ID NO:6. For example, some embodiments include amino acid sequences that have at least about 80%, at least about 85%, at least about 90%, or at least about 95% sequence identity to SEQ ID NO: 2, SEQ ID NO:4, or SEQ ID NO:6. Examples of such sequence identity include about 80, about 81, about 82, about 83, about 84, about 85, about 86, about 87, about 88, about 89, about 90, about 91, about 92, about 93, about 94, about 95, about 96, about 97, about 98, about 99, and about 100%.

In certain embodiments, administration of a nucleic acid molecule results in expression of the encoded inventive polypeptide. In other embodiments, the thermal sensitive ion channel or variant thereof portion of the inventive polypeptide resides in the membrane of a cell and the domain 5 of kininogen 1 or variant or fragment thereof portion of the inventive polypeptide resides in a cell space or compartment that comprises ferritin (e.g., the cytosol). In certain embodiments, and without being bound by theory, ferritin (e.g., endogenous ferritin) is in close proximity to the inventive polypeptide (e.g., because, in some embodiments, ferritin binds to or is associated with the domain 5 of kininogen 1 or variant or fragment thereof portion of the inventive polypeptide). Without being bound by theory, the close proximity of ferritin can sometimes permit the application of heat (e.g., by application of an electromagnetic field) or mechanical force (e.g., by the application of a static magnetic field) to the inventive polypeptide (and by implication the membrane of cell in which the inventive polypeptide resides) via the iron in ferritin. Thus, in some embodiments and without being bound by theory, the close proximity of ferritin to the inventive polypeptide permits modulation of certain aspects of the cell membrane and/or cell.

In some embodiments, the inventive polypeptide can be modulated by temperature (e.g., directly or indirectly). For example, modulation of the inventive polypeptide can modulate the membrane potential, the ion flow, or both. Modulation of the membrane potential can, in some instances, result in polarization, repolarization, depolarization, or hyperpolarization (e.g., in a neuron, a glial cell, a cancer cell, an airway epithelial cell, or an immune cell). For example, modulation of the inventive polypeptide can open, partially open, close, partially close, or reverse ion flow in the ion channel portion of the inventive polypeptide when the temperature is increased (e.g., directly or indirectly, such as with application of RF or static magnetic field) or when the temperature is decreased. In some embodiments, the inventive polypeptide can modulate the flow of $Ca^{2+}$, $Mg^{2+}$, $Ba^{2+}$, $Be^{2+}$, $I^-$, $Br^-$, $Cl^-$, $F^-$, $Tl^+$, $Cs^+$, $Rb^+$, $K^+$, $Na^+$, $Li^+$, $H^+$, or combinations thereof. In some embodiments, the inventive polypeptide can modulate the flow of $Ca^{2+}$, $Mg^{2+}$, $I^-$, $Cl^-$, $Tl^+$, $Tl^+$, $Na^+$, or combinations thereof. In certain embodiments, the inventive polypeptide can modulate the flow of one or more ions (e.g., it can modulate both $K^+$ and $Na^+$). Modulation of ion flow by an inventive polypeptide includes, but is not limited to increasing ion flow, decreasing ion flow, starting ion flow, stopping ion flow, or reversing the direction of ion flow.

Some embodiments of the invention include a nucleic acid molecule that encodes the inventive polypeptide. In certain embodiments, the nucleic acid molecule comprises a vector or a plasmid. In certain embodiments, the nucleic acid molecule comprises a transcription regulator, including but not limited to promoter sequences or enhancer sequences. In other embodiments, the nucleic acid molecule comprises tissue specific promoter, a cell-specific promoter, UAS promoter, or sensory neuron promoter et101.2. In still other embodiments, the nucleic acid molecule comprises a gene delivery vector, including, but not limited to, a lentivirus, an adenovirus, an adeno-associated virus, a retrovirus, herpes simplex virus, vaccinia virus, or a self inactivating viral vector. In other embodiments, the genome can be edited with CRISPR-Cas9. In certain embodiments, the nucleic acid molecule is in a cell, such as an insect (e.g., Sf9), a mammalian cell (e.g., CHO or HEK), or an avian cell (e.g., primary cell culture or EB66(R)).

Some embodiments of the nucleic acid molecules include variants of SEQ ID NO:1, SEQ ID NO:3, or SEQ ID NO:5. For example, some embodiments include nucleic acid sequences that have at least about 80%, at least about 85%, at least about 90%, or at least about 95% sequence identity to SEQ ID NO:1, SEQ ID NO:3, or SEQ ID NO:5. Examples of such percent sequence identity include about 80, about 81, about 82, about 83, about 84, about 85, about 86, about 87, about 88, about 89, about 90, about 91, about 92, about 93, about 94, about 95, about 96, about 97, about 98, about 99, and about 100%.

The amino acid sequence identity or nucleic acid sequence identity (e.g., percent identity) can be determined by any suitable method, such as using BLAST, BLAST-2, ALIGN, ALIGN-2, or Megalign software. Unless otherwise indicated, the amino acid sequence identity (e.g., percent identity) or nucleic acid sequence identity (e.g., percent identity) is determined using BLAST-2.

As modifications or changes may be made in the structure of the nucleic acid molecules and/or inventive polypeptides of the present invention, while obtaining molecules having similar or improved characteristics, such biologically functional equivalents are also encompassed within some embodiments of the present invention. In certain instances, the biological functional equivalent may comprise a nucleic acid that has been engineered to contain distinct sequences while at the same time retaining the capacity to encode the desired inventive polypeptide. This can be accomplished owing to the degeneracy of the genetic code (i.e., the presence of multiple codons) which encode for the same amino acids. In one example, one of ordinary skill in the art may wish to introduce a restriction enzyme recognition sequence into a nucleic acid sequence while not disturbing the ability of that polynucleotide to encode a protein.

In another example, a nucleic acid molecule can be engineered to contain certain sequences that result in (and encode) a biological functional equivalent with more significant changes. In some embodiments, certain amino acids may be substituted for other amino acids in a protein structure without appreciable loss of desired function such as, for example, the thermal sensitivity or ferritin binding. So-called "conservative" changes do not disrupt the desired biological activity of the protein, as the structural change is not one that impinges on the protein's ability to carry out its desired functions. Some embodiments of the present invention encompass various changes that may be made in the sequence of nucleic acid molecules and in the sequence of inventive polypeptides disclosed herein.

In terms of functional equivalents, it is well understood by the skilled artisan that, inherent in the definition of a "biologically functional equivalent" polypeptide or polynucleotide, is the concept that there is a limit to the number of changes that may be made within a defined portion of the molecule while retaining a molecule with an acceptable level of desired biological activity, such as, for example, the thermal sensitivity or ferritin binding. Biologically functional equivalents are thus defined herein as those polypeptides (and nucleic acid molecules) in which selected amino acids (or codons) may be substituted.

In general, the shorter the length of the molecule, the fewer the changes that can be made within the molecule while retaining function. Longer domains may have an intermediate number of changes. The full-length protein will have the most tolerance for a larger number of changes. However, certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, or the like. An analysis of the size, shape or type of the amino acid side-chain substituents reveals that arginine, lysine or histidine are all positively charged residues; that alanine, glycine or serine are all of similar size; or that phenylalanine, tryptophan or tyrosine all have a generally similar shape. Therefore, based upon these considerations, arginine, lysine or histidine; alanine, glycine or serine; or phenylalanine, tryptophan or tyrosine; are defined herein as biologically functional equivalents. Although not grouped here, other amino acids may provide functionally equivalent polypeptides.

The hydropathic index of amino acids may also be considered. Each amino acid has been assigned a hydropathic index on the basis of their hydrophobicity or charge characteristics, these are: isoleucine (+4.5); valine (+4.2); Leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); or arginine (−4.5). Hydropathic amino acid index can be used to confer interactive biological function on a protein. In some instances, certain amino acids may be substituted for other amino acids having a similar hydropathic index or score or still retain a similar biological activity. In making changes based upon the hydropathic index, the substitution of amino acids with hydropathic indices can be within ±2 or within ±1, or within ±0.5.

The substitution of like amino acids can also be made on the basis of hydrophilicity, particularly where the biological functional equivalent polypeptide or peptide thereby created is intended for use in immunological embodiments, as in certain embodiments of the present invention. U.S. Pat. No. 4,554,101 states that the greatest local average hydrophilicity of a polypeptide, as governed by the hydrophilicity of its adjacent amino acids, can correlate with its immunogenicity or antigenicity (i.e., with a biological property of the polypeptide).

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids with hydrophilicity values can be within ±2, or within ±1, or within ±0.5.

Conservatively substituted sequence indicates that a given amino acid residue is replaced by a residue having similar physiochemical characteristics. Examples of conservative substitutions include substitution of one aliphatic residue for another, such as Be, Val, Leu, or Ala for one another, or substitutions of one polar residue for another, such as between Lys and Arg; Glu and Asp; or Gln and Asn. Other such conservative substitutions include, for example, substitutions of entire regions having similar hydrophobicity characteristics.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like.

Tables A and B. Amino Acid Designations and Codon Table

TABLE A

| Amino Acid Designations | | |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

TABLE B

| Codons for Amino Acids |
|---|
| GCA GCC GCG GCU |
| UGC UGU |
| GAC GAU |
| GAA GAG |

TABLE B-continued

Codons for Amino Acids

UUC UUU

GGA GGC GGG GGU

CAC CAU

AUA AUC AUU

AAA AAG

UUA UUG CUA CUC CUG CUU

AUG

AAC AAU

CCA CCC CCG CCU

CAA CAG

AGA AGG CGA CGC CGG CGU

AGC AGU UCA UCC UCG UCU

ACA ACC ACG ACU

GUA GUC GUG GUU

UGG

UAC UAU

The term "functionally equivalent codon" is used herein to refer to codons that encode the same amino acid, such as the six codons for arginine or serine, and also refers to codons that encode biologically equivalent amino acids (see Codon Table, above).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological activity where polypeptide expression is concerned. The addition of terminal sequences particularly applies to nucleic acid sequences that may, for example, include various non-coding sequences flanking either of the 5' or 3' portions of the coding region or may include various internal sequences, (i.e., introns) which are known to occur within genes.

The present invention, in some aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified or unusual amino acids. A table of exemplary, but not limiting, modified or unusual amino acids is provided in Table C.

TABLE C

Modified or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

The presently-disclosed subject matter further includes a method of producing an inventive polypeptide. Eukaryotic expression systems include plant-based systems; insect cell systems via recombinant baculoviruses; whole insect systems via recombinant baculoviruses; genetically engineered yeast systems, including but not limited to *Saccharomyces* sp. and *Picchia* spp.; and mammalian cell systems, including but not limited to Chinese hamster ovary cells or other cell lines commonly used for industrial scale expression of recombinant proteins. In some embodiments, useful plant-based expression systems can include transgenic plant systems. In some embodiments, useful plant-based expression systems can include transplastomic plant systems.

In some embodiments, a method of producing the inventive polypeptide includes providing a host cell comprising a nucleic acid molecule, as disclosed herein, operatively linked to a promoter operable under conditions whereby the encoded polypeptide is expressed; and recovering the polypeptide from the host cell.

One or more inventive polypeptides or nucleic acid molecules can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more inventive polypeptides or nucleic acid molecules can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%. Some embodiments of the present invention include compositions comprising one or more inventive polypeptides or one or more nucleic acid molecules. In certain embodiments, the composition is a pharmaceutical composition, such as compositions that are suitable for administration to animals (e.g., mammals, primates, monkeys, humans, canine, porcine, mice, rabbits, or rats).

Compositions Including Pharmaceutical Compositions

One or more inventive polypeptides or nucleic acid molecules can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more inventive polypeptides or nucleic acid molecules can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more inventive polypeptides or one or more nucleic acid molecules. In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

In some embodiments, one or more inventive polypeptides or one or more nucleic acid molecules can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more inventive polypeptides or one or more or nucleic acid molecules) substantially immediately upon the administration or any substantially predetermined time or time after administration. Such formulations can include, for example, controlled release formulations such as various controlled release compositions and coatings.

Other embodiments of the invention can include methods of administering an organism. In some embodiments, the composition or pharmaceutical composition comprises at least one inventive polypeptide or at least one nucleic acid molecule which can be administered to an animal (e.g., mammals, primates, monkeys, or humans) in an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention can be administered in combination with one or more other therapeutic agents for a given disease or disorder.

In some embodiments, the compositions can include a pharmaceutically acceptable carrier and, in addition, can include other medicinal agents, pharmaceutical agents, carriers, adjuvants, diluents, liposomes, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. Carriers can also include, in certain instances, a liposome or liposome system. In other embodiments, the one or more excipients can include, but are not limited to water, saline, dextrose, glycerol, ethanol, or the like, and combinations thereof. In some embodiments, liposomes are used to transport or deliver (e.g., as a carrier for) the nucleic acid molecule. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Parenteral administration, if used, is generally characterized by injection. Sterile injectables can be prepared in conventional forms, either as liquid solutions or suspensions, solid forms suitable for solution or suspension in liquid prior to injection, or as emulsions.

Administration Routes

The inventive polypeptides or nucleic acid molecules can be administered to animals by any number of suitable administration routes or formulations. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration.

In some embodiments, electroporation and any other similar technique (e.g., chemical-poration) can be used as an administrative route. In other embodiments, the administration route can include the use of nucleases (e.g., to administer the nucleic acid molecule) such as Meganucleases, Zinc Finger Nucleases, Transcription Activator-Like Effector Nucleases, and CRISPR/Cas9 systems; the use of nucleases can, for example, create specific double-strand breaks at the target locus that trigger DNA repair mechanisms; these corrections can sometimes result in two types of genome modifications: constitutive Knockouts (e.g., through non-homologous end joining) and Knockins (e.g., through homologous recombination).

In some embodiments, the choice of administration route can depend on the inventive polypeptide or nucleic acid molecule identity (e.g., the physical and chemical properties of the inventive polypeptide or nucleic acid molecule) as well as the age and weight of the animal, the particular disease or disorder, and the severity of the disease or disorder. Of course, combinations of administration routes can be administered, as desired.

Some embodiments of the invention include a method for providing a subject with a composition comprising an inventive polypeptide or a nucleic acid molecule described herein (e.g., a pharmaceutical composition) which comprises one or more administrations of one or more such compositions; the compositions may be the same or different if there is more than one administration.

Application of a Static Magnetic Field or of an Electromagnetic Field

Some embodiments of the invention include methods that comprise application of a static magnetic field or of an electromagnetic field. In certain embodiments, a static magnetic field is applied to, for example, provide a mechanical force on the ferritin bound to the inventive polypeptide. Any suitable static magnetic field can be applied and can, in some instances, be adjusted depending on one or more factors including, but not limited to (as applicable) the inventive polypeptide, the cell that comprises the inventive polypeptide, the tissue that comprises the inventive polypeptide, the disease or disorder, the desired mechanical force, or the equipment used to apply the static magnetic field. The applied static magnetic field can be any suitable strength, such as, but not limited to, from about 0.1 µT to about 50 T, 0.1 µT to about 25 T, 0.1 µT to about 21 T, from about 0.1 µT to about 100 mT, from about 1 µT to about 50 T, from about 1 µT to about 25 T, from about 1 µT to about 21 T, from about 1 µT to about 100 mT, from about 10 µT to about 100 mT, from about 10 µT to about 50 mT, about 0.1 µT, 0.5 µT, about 1 mT, about 10 mT, about 50 mT, about 100 mT, about 500 mT, about 21 T, about 25 T, or about 50 T. The units of the static magnetic field can be Tesla or Gauss (100 G=10 mT). The applied static magnetic field in some embodiments results in a mechanical force from about 0.01 pN to about 500 pN, 0.01 pN to about 250 pN, 0.01 pN to about 210 pN, from about 0.05 pN to about 1.5 pN, from about 0.1 pN to about 1 pN, from about 0.1 pN to about 0.5 pN, from about 0.2 pN to about 0.4 pN, about 0.01 pN, about 0.05 pN, 0.1 pN, about 0.15 pN, about 0.2 pN, about 0.25 pN, about 0.3 pN, about 0.35 pN, about 0.4 pN, about 0.45, pN, about 0.5 pN, about 0.6 pN, about 0.7 pN, about 0.8 pN, about 1 pN, about 1.2 pN, about 1.5 pN, about 2 pN, about 5 pN, about 7 pN, about 210 pN, about 250 pN, or about 500 pN. In some instances, the static magnetic field can be steady state or can be pulsed, to, for example, achieve the desired effect on the inventive polypeptide (e.g., mechanical force to open or close a channel) or cell.

In certain embodiments an electromagnetic field is applied to, for example, provide heat to the inventive polypeptide (e.g., via bound ferritin) or cell (e.g., via ferritin bound to the inventive polypeptide). Any suitable electromagnetic field (e.g., any suitable frequency (or combinations of frequencies), any suitable amplitude(s), or any suitable pulse sequence or steady state application) can be applied and can, in some instances, be adjusted depending on one or more factors including, but not limited to (as applicable) the inventive polypeptide, the cell that comprises the inventive polypeptide, the tissue that comprises the inventive polypeptide, the disease or disorder, the desired amount of heat, or the equipment used to apply the electromagnetic field. The electromagnetic field can be any suitable frequency or amplitude. In some embodiments, the electromagnetic field frequency can be from about 0.01 Hz to about 300 GHz, from about 100 Hz to about 10 GHz, from about 1 kHz to about 10 GHz, from about 10 kHz to about 10 GHz, from about 100 Hz to about 1 GHz, from about 1 kHz to about 1 GHz, from about 10 kHz to about 1 GHz, from about 10 kHz to about 500 MHz, from about 100 kHz to about 1 GHz, or from about 100 kHz to about 500 MHz.

In some instances, the electromagnetic field can be steady state or can be pulsed, to, for example, achieve the desired effect on the inventive polypeptide (e.g., heating (e.g., with kHz range frequencies) to open an ion channel, to close an ion channel, to reverse ion flow in an ion channel, to cause membrane polarization, to cause membrane repolarization, to cause membrane depolarization, or to cause membrane hyperpolarization, or to create spatial patterns (e.g., with GHz range frequencies)). In some embodiments, pulsed electromagnetic fields may be synchronized with imaging devices such as, but not limited to an MRI, which can use, for example, a repeated gradient echo sequence.

Figure 1:
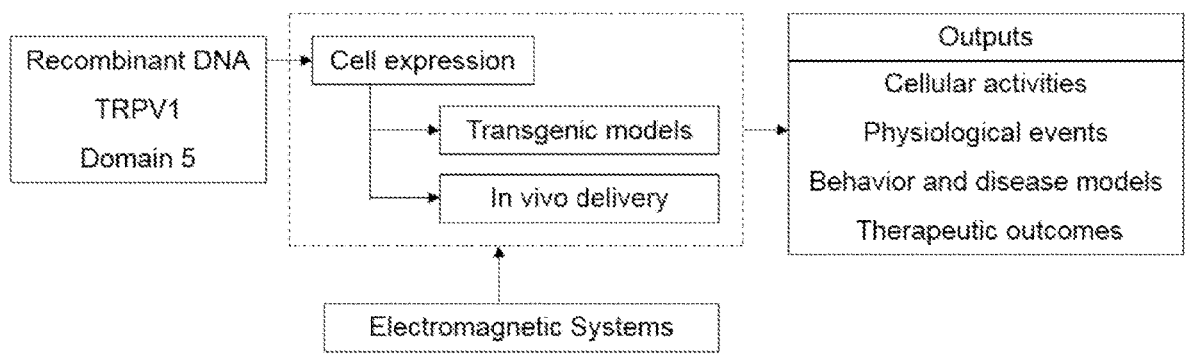
FIG. 1 is a schematic diagram of some embodiments of the methods and/or systems disclosed herein. In some instances, cells and organ systems can be modified through genetic techniques. In certain embodiments, the static magnetic field(s) or electromagnetic field(s) can be applied by any suitable system (referred to as "EM system"). Observables can include but are not limited to cellular, physiological, behavioral and therapeutic events.
Figure 2:
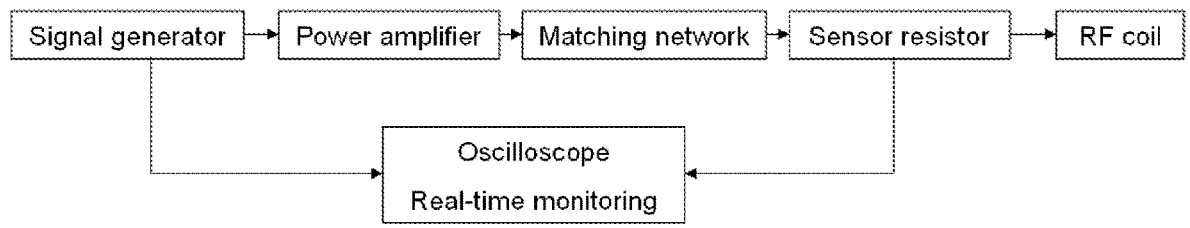
FIG. 2 is an example of block diagram of a system for applying static magnetic field(s) or electromagnetic field(s) (referred to as "EM system") with real time monitoring.
Figure 3:
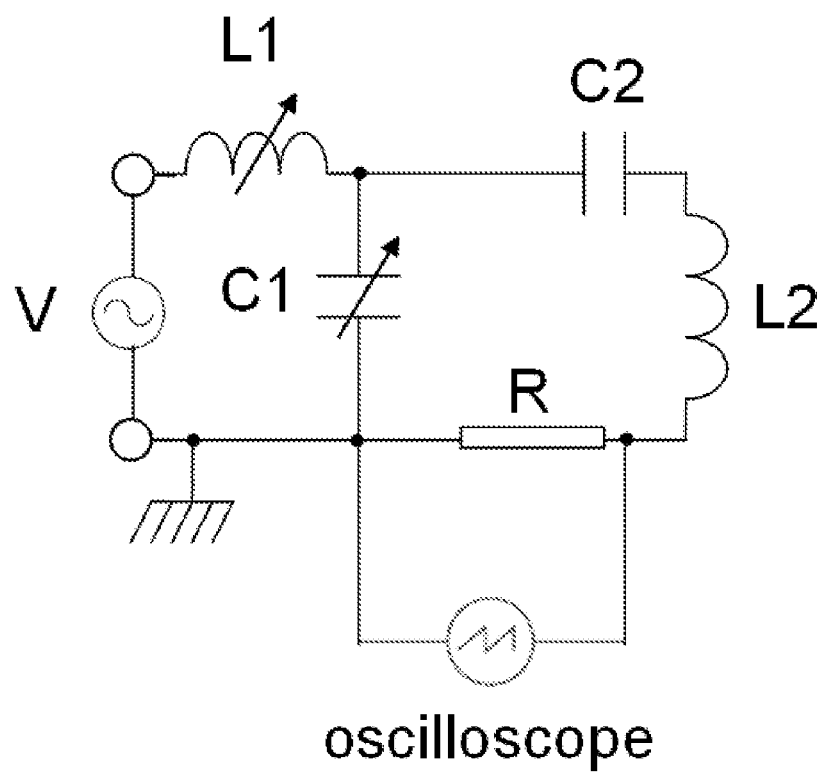
FIG. 3 is an example of a LC circuit that could be used with a system for applying static magnetic field(s) or electromagnetic field(s) (referred to as "EM system").
Figure 4:
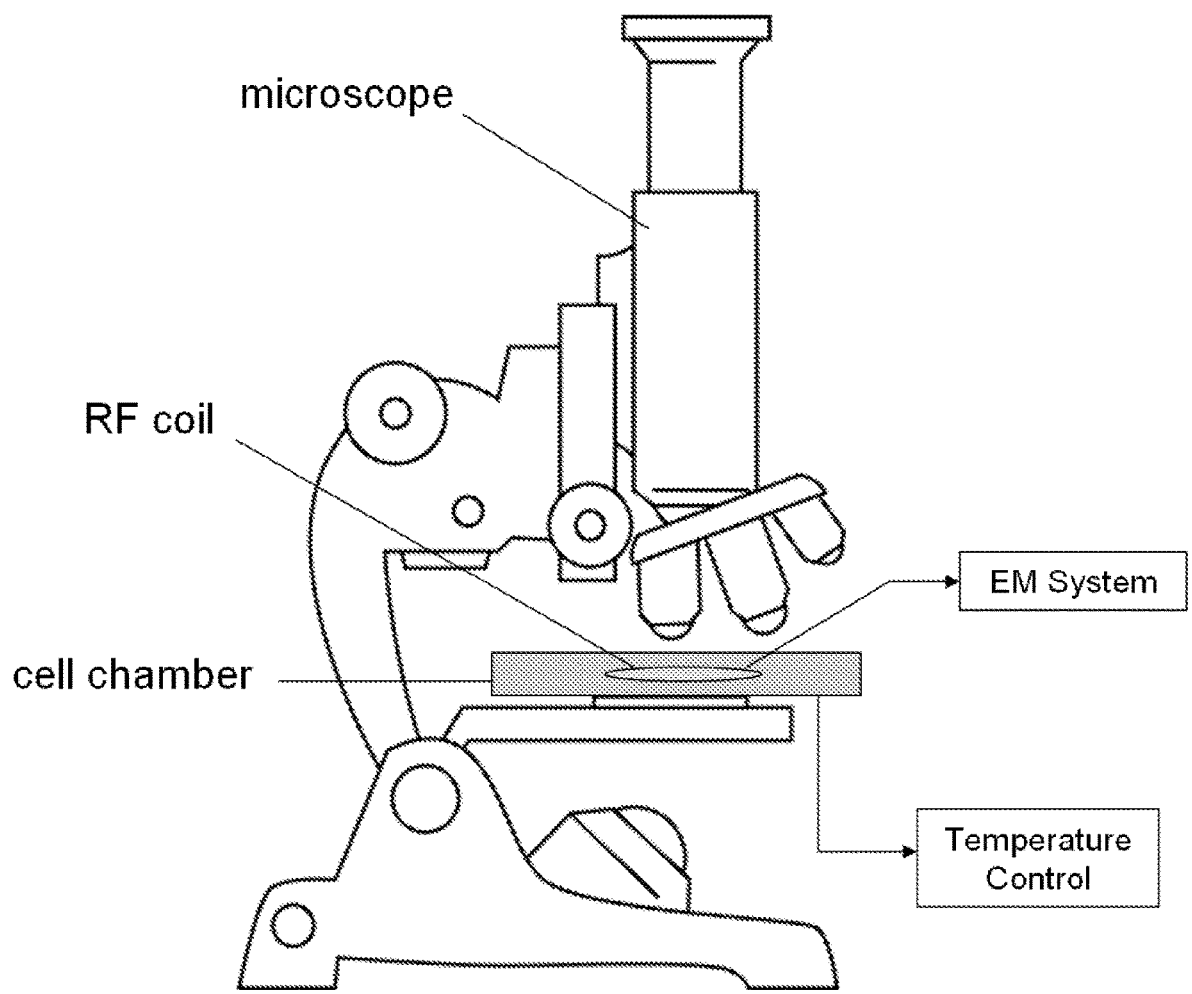
FIG. 4 is an example of a live cell imaging system with microscope and real time system for applying static magnetic field(s) or electromagnetic field(s) (referred to as "EM system").
Figure 5:
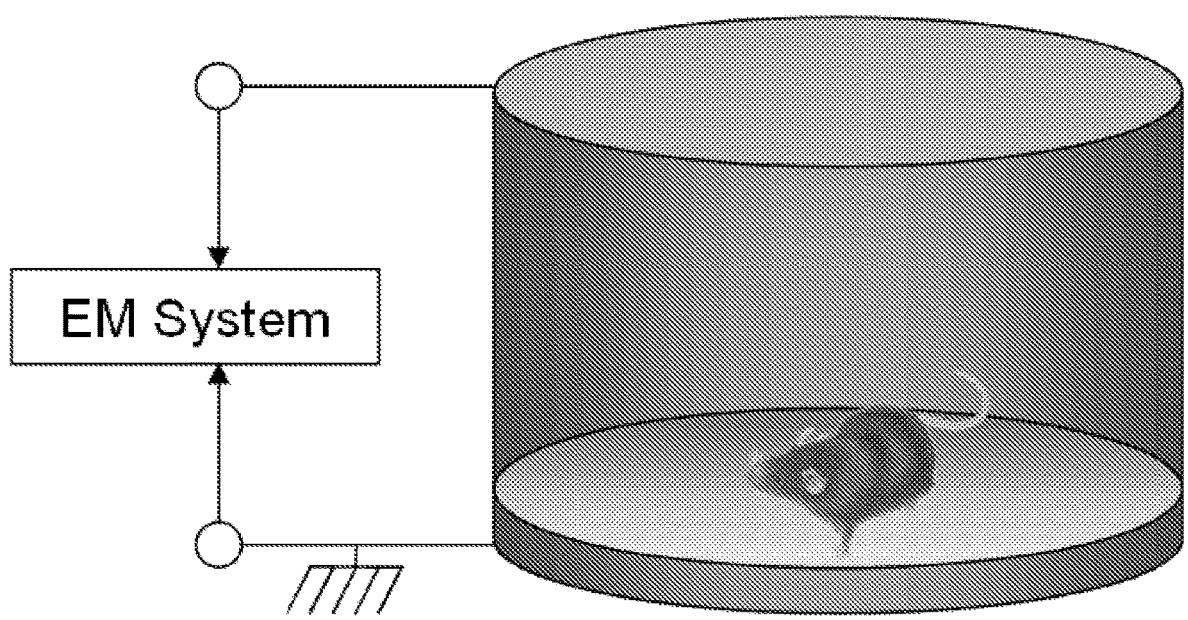
FIG. 5 is an example of a system for applying static magnetic field(s) or electromagnetic field(s) (referred to as "EM system") for animal studies. The cage sits inside a RF coil.
Figure 6:
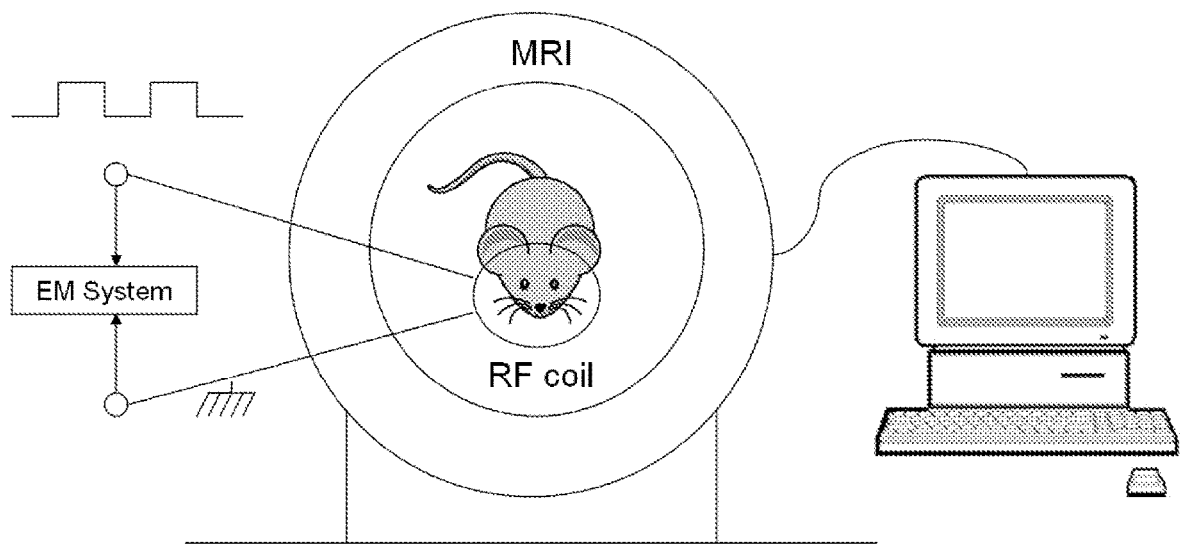
FIG. 6 is an example of MRI used to measure animal neural activities induced by static magnetic fields or by electromagnetic fields (e.g., via the "EM system" shown) in an animal after being delivered an inventive polypeptide (e.g., via a lentivector). In some embodiments, the static magnetic field(s) or electromagnetic field(s) can be programmed and/or controlled by the operator (e.g., via a pre-existing system in the MRI or by additional systems not originally found in the MRI).

Any suitable machine or system can be used generate and/or deliver the static magnetic field or electromagnetic field. In some embodiments, the machine or system can comprise one or more of the following, including but not limited to, an nuclear magnetic resonance machine, a magnetic resonance imaging machine, an electromagnet, an RF coil (e.g., a surface coil, a paired saddle coil, a Helmholtz paired coil, or a birdcage coil), an RF cage (e.g., a paired saddle coil, a Helmholtz paired coil, or a birdcage coil), an antenna, a system shown in FIG. 2, a system similar to that shown in FIG. 2, a system shown in FIG. 3, a system similar to that shown in FIG. 3, a system shown in FIG. 4, a system similar to that shown in FIG. 4, a system shown in FIG. 5, a system similar to that shown in FIG. 5, a system shown in FIG. 6, or a system similar to that shown in FIG. 6.

In some embodiments, an MRI is an adequate mechanism to deliver electromagnetic fields. In other embodiments, the electromagnetic field can be delivered into cell cultures and tissues with a simple LC resonator (RF coil, such as that found in FIG. 3) or more sophisticated RF transmit systems. In certain embodiments, the temporal waveform of the electromagnetic field can be pulsed or continuous and can be programmed and controlled by a signal generator. In still other embodiments, the spatial pattern of the electromagnetic field can be manipulated with array of coils and advanced metamaterials.

In one embodiment, the signal generator provides a sinusoidal wave of specific frequency and voltage to the power amplifier; the amplification is constant at 50 dBm. In this embodiment, the output of the generator is adjusted to drive the RF coil with enough current to produce the required magnetic field. Still referring to this embodiment, the output impedance of the amplifier is at 50 Ohms (purely resistive load); however the RF coil impedance is different. In certain embodiments, the power amplifier has minimum reflected power when the load impedance (the coil in this case) is matched to the impedance of the amplifier. For example, the impedance of a two-turn RF coil operating around 60 MHz is $$R_{total}=R+i\omega L$$

where R is on the order of 0.5 Ohms and it includes layout losses on printed circuit boards, sample loading, radiation losses and the current sense resistor; $\omega=2\pi f$ and $f=60$ MHz, and $L=240$ nH as measured by an inductance meter. When on resonance, the output of the generator is matched to the input of the RF coil with high Q and low reflected power, in some embodiments. The matching network can include capacitors and the tuning coil. For live cell imaging, the coils can, in some instances, be made small and fitted inside a temperature controlled cell chambers under the microscope.

In some embodiments, the transmit coil can be made large to enclose a cage where animal behavior is studied. In other embodiments, the transmit coil can be wireless and wearable on the head or body of the animal.

In certain embodiments, the modulation of a cell induced by the static magnetic field or by the electromagnetic field can be monitored. For example, neuronal activities induced by the interactions between electromagnetic field and inventive polypeptide can be captured (e.g., in vivo) with an MRI, a CT or an ultrasound. In one embodiment, pulsed electromagnetic fields or pulsed static fields are transmitted to the brain while magnetic resonance images are acquired simultaneously; these RF waves can be different frequencies from the Larmor frequency and thus would, in some instances, minimize interference with the MRI.

In some instances, a certain spatial pattern of electromagnetic fields (e.g., RF fields) is desired for achieving more anatomically localized membrane channel activation. Such a gated delivery of electromagnetic field (e.g., RF field) energy can, in certain embodiments, be achieved with array of coils and/or in combination with metamaterials. In some embodiments, spatial localization can be achieved at higher frequencies, such as, for example, in the GHz range.

In certain embodiments, all electromagnetic field frequencies can be produced using an MRI machine; the electromagnetic field frequency may be produced by a separate coil that is not part of an unmodified MRI machine. In some embodiments, a separate coil may be used in an MRI machine to achieve better flexibility in controlling the duration and strength of electromagnetic field. In certain instances, if the electromagnetic field frequency is to be produced by coils onboard the MRI machine, then the Larmor frequency can be used. For example, on a 3 T MRI scanner, the Larmor frequency of a proton is about 128 MHz; the frequency scales linearly with the static field strength of the MRI scanner.

In other embodiments, the static magnetic field or electromagnetic field can be applied using a wired mechanism or using a wireless mechanism.

Methods for Modulating a Cell

Some embodiments of the invention include a method for modulating at least one cell comprising administering a nucleic acid molecule (e.g., which encodes any inventive polypeptide disclosed herein) to at least one cell and applying a static magnetic field or an electromagnetic field, wherein the cell is modulated upon applying the static magnetic field or the electromagnetic field. Administering the nucleic acid molecule can include any suitable method, including those disclosed herein. Application of the static magnetic field or of the electromagnetic field, can be any such suitable field (e.g., those disclosed herein) or by any suitable means (e.g., those disclosed herein). In certain embodiments, the electromagnetic field has a frequency from about 0.01 Hz to about 300 GHz.

In certain embodiments, administration of a nucleic acid molecule results in expression of the encoded inventive polypeptide. In other embodiments, the thermal sensitive ion channel or variant thereof portion of the inventive polypeptide resides in the membrane of a cell and the domain 5 of kininogen 1 or variant or fragment thereof portion of the inventive polypeptide resides in a cell space or compartment that comprises ferritin (e.g., the cytosol). In certain embodiments, and without being bound by theory, ferritin (e.g., endogenous ferritin) is in close proximity to the inventive polypeptide (e.g., because, in some embodiments, ferritin binds to or is associated with the domain 5 of kininogen 1 or variant or fragment thereof portion of the inventive polypeptide). Without being bound by theory, the close proximity of ferritin can sometimes permit the application of heat (e.g., by application of an electromagnetic field) or mechanical force (e.g., by the application of a static magnetic field) to the inventive polypeptide (and by implication the membrane of cell in which the inventive polypeptide resides) via the iron in ferritin. Thus, in some embodiments and without being bound by theory, the close proximity of ferritin to the inventive polypeptide permits modulation of certain aspects of the cell membrane and/or cell.

In some embodiments, modulating the cell comprises modulating ion flow across a cell membrane. In certain embodiments, the ion is $K^+$, $Na^+$, $Ca^{2+}$, $Mg^{2+}$, $Cl^-$, or combinations thereof. In other embodiments, the ion flow into the at least one cell is increased or decreased or the ion flow is reversed. In other embodiments, modulating the cell comprises hyperpolarizing a cell membrane in the cell or polarizing a cell membrane in the cell.

In some embodiment, the nucleic acid molecule is part of a vector or a virus. In certain embodiments, the at least one cell can be in vitro or in ovo. In other embodiments, the at least one cell can be part of an organ and/or part of a multicellular organism. In still other embodiments, the at least one cell can be part of an animal (e.g., murine, zebrafish, chicken embryo, or human). In certain embodiments, the at least one cell can be a neuron, a glial cell, a cancer cell, an airway epithelial cell, or an immune cell.

In some embodiments, the administering can be parenteral administration, a mucosal administration, intravenous administration, subcutaneous administration, topical administration, intradermal administration, oral administration, sublingual administration, intranasal administration, or intramuscular administration.

Methods for Treating Diseases or Disorders

Some embodiments of the invention include a method for treating an animal for a disease or a disorder comprising administering a nucleic acid molecule (e.g., which encodes any inventive polypeptide disclosed herein) to the animal and applying a static magnetic field or an electromagnetic field to the animal, wherein at least one cell in the animal is modulated upon applying the static magnetic field or the electromagnetic field, and the modulation treats the disease or disorder. Administering the nucleic acid molecule can include any suitable method, including those disclosed herein. Application of the static magnetic field or of the electromagnetic field, can be any such suitable field (e.g., those disclosed herein) or by any suitable means (e.g., those disclosed herein). In certain embodiments, the static magnetic field can be from about 0.1 mT to about 50 T or the electromagnetic field can have a frequency from about 0.01 Hz to about 300 GHz.

In certain embodiments, administration of a nucleic acid molecule results in expression of the encoded inventive polypeptide. In other embodiments, the thermal sensitive ion channel or variant thereof portion of the inventive polypeptide resides in the membrane of a cell and the domain 5 of kininogen 1 or variant or fragment thereof portion of the inventive polypeptide resides in a cell space or compartment that comprises ferritin (e.g., the cytosol). In certain embodiments, and without being bound by theory, ferritin (e.g., endogenous ferritin) is in close proximity to the inventive polypeptide (e.g., because, in some embodiments, ferritin binds to or is associated with the domain 5 of kininogen 1 or variant or fragment thereof portion of the inventive polypeptide). Without being bound by theory, the close proximity of ferritin can sometimes permit the application of heat (e.g., by application of an electromagnetic field) or mechanical force (e.g., by the application of a static magnetic field) to the inventive polypeptide (and by implication the membrane of cell in which the inventive polypeptide resides) via the iron in ferritin. Thus, in some embodiments and without being bound by theory, the close proximity of ferritin to the inventive polypeptide permits modulation of certain aspects of the cell membrane and/or cell.

In some embodiments, modulating the cell comprises modulating ion flow across a cell membrane. In certain embodiments, the ion can be $K^+$, $Na^+$, $Ca^{2+}$, $Mg^{2+}$, $Cl^-$, or combinations thereof. In other embodiments, the ion flow into the at least one cell can be increased or decreased or the ion flow can be reversed. In other embodiments, modulating the cell comprises polarizing, depolarizing, repolarizing, or hyperpolarizing a cell membrane in the cell.

In some embodiment, the nucleic acid molecule is part of a vector or a virus. In other embodiments, the at least one cell can be part of an organ (e.g., the brain). In certain embodiments, the at least one cell can be a neuron, a glial cell, a cancer cell, an airway epithelial cell, or an immune cell.

In some embodiments, the administering can be parenteral administration, a mucosal administration, intravenous administration, subcutaneous administration, topical administration, intradermal administration, oral administration, sublingual administration, intranasal administration, or intramuscular administration.

Diseases or disorders that can be treated in the animal (e.g., mammals, porcine, canine, avian (e.g., chicken), bovine, feline, primates, monkeys, rabbits, murine, and humans) include, but are not limited to complex regional pain syndrome, pain, chronic pain, post traumatic stress disorder, epilepsy, movement disorders, Parkinson's disease, and cystic fibrosis. Animals that can be treated include but are not limited to mammals, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., a prophylactic treatment).

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. For example, treating pain (or a pain related disease or disorder, such as chronic pain syndrome, complex regional pain syndrome, or chronic pain) does not mean that all pain is necessary gone, but that there is at least some diminution of pain. As used herein, reference to "treating" an animal includes but is not limited to prophylactic treatment and therapeutic treatment. Any of the compositions (e.g., pharmaceutical compositions) described herein can be used to treat an animal. Any application of the static magnetic field (e.g., those disclosed herein) or of the electromagnetic field (e.g., those disclosed herein) can be used to treat an animal. In some embodiments, treating does not include prophylactic treatment (e.g., preventing or ameliorating future disease or disorder).

In some embodiments, the method of treatment comprises administering a nucleic acid molecule that can encode a polypeptide comprising TRPV1, TRPV4, ANO1, TREK-1, a variant of TRPV1, a variant of TRVP4, a variant of ANO1 or a variant of TREK-1. In other embodiments, the nucleic acid molecule can encode a polypeptide comprising a domain 5 of kininogen 1 (e.g., SEQ ID NO: 13) or a fragment of a domain 5 of kininogen 1 (e.g., a nucleic acid encoding SEQ ID NO: 15, SEQ ID NO: 16, SEQ ID NO: 17, SEQ ID NO: 18, SEQ ID NO: 19, or SEQ ID NO: 20). In other embodiments, the nucleic acid molecule can encode a polypeptide comprising an ANO1 (e.g., SEQ ID NO: 11) or a variant of ANO1, and the disease or disorder that is treated is cystic fibrosis. In yet other embodiments, the nucleic acid molecule encodes a polypeptide comprising an TRPV1 (e.g., SEQ ID NO: 7 or SEQ ID NO: 9) or a variant of TRPV1, and the disease or disorder that is treated is pain, chronic pain syndrome, complex regional pain syndrome, or chronic pain.

Treatment of an animal can occur using any suitable administration method (such as those disclosed herein), using any suitable amount of inventive polypeptide or nucleic acid molecule (such as those disclosed herein), and using any suitable static magnetic field (e.g., those disclosed herein) or electromagnetic field (e.g., those disclosed herein). Some embodiments of the invention include a method for administering to a subject (e.g., an animal such as a human or primate) a composition described herein (e.g., a pharmaceutical composition) which comprises one or more administrations of one or more such compositions; the compositions may be the same or different if there is more than one administration. Some embodiments of the invention include a method comprising applying any suitable static magnetic field (e.g., those disclosed herein) or electromagnetic field (e.g., those disclosed herein) to a subject (e.g., an animal such as a human or primate) which comprises one or more applications of one or more such suitable static magnetic field or electromagnetic field; the applications may be the same or different if there is more than one administration (e.g., the first application can be a static magnetic field and the second application can be an electromagnetic field or the first application can be an electromagnetic field of one frequency and the second application can be an electromagnetic field of a different frequency).

In some embodiments, the method of treatment comprises administering an effective amount of a composition (e.g., such as those compositions and pharmaceutical composition described herein). As used herein, the term "effective amount" refers to a dosage or a series of dosages sufficient to affect treatment (e.g., to treat a disease or disorder) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of the inventive polypeptide or nucleic acid molecule (which can be administered to an animal such as mammals, primates, monkeys or humans) can be an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg.

In some embodiments, the method of treatment includes applying an effective amount of one or more applications of static magnetic field or electromagnetic field (e.g., such as those described herein). As used herein, the term "effective amount" refers to a single application or a series of applications (which may be the same or different) sufficient to affect treatment (e.g., to treat a disease or disorder) in an animal.

In some embodiments, the treatments disclosed herein can include use of other drugs (e.g., antibiotics) or therapies for treating disease. For example, antibiotics can be used to treat infections and can be combined to treat disease (e.g., infections).

The presently-disclosed subject matter is further illustrated by the following specific but non-limiting examples. The following examples may include compilations of data that are representative of data gathered at various times during the course of development and experimentation related to the present invention.

EXAMPLES

The examples and methods below should be considered to be exemplary only and not construed to be limiting upon the present disclosure. Other polypeptides and nucleic acid molecules can be designed and made. Other methods and variations of the provided methods may be used, in certain embodiments, to measure the same physical properties or characteristics. Additional examples of polypeptides, nucleic acid molecules, and methods may be found herein.

Example Set 1

Design and Cloning of TRVP1.D5

Cloning of Transient Receptor Potential channel Vanilloid 1 (TRPV1—also referred herein to as TRPv1) and the fusion protein TRPV1.D5 (also referred to herein as TRPv1.D5)

TRPV1: RNA was extracted from mouse spinal cord tissue and reverse transcribed into cDNA. 1 μg of cDNA was used in a PCR reaction to amplified full length TRPV1. The 5' primer used introduced an Spe1 restriction endonuclease site. The 3' TRPV1 primer abolished the stop codon and introduced an Xba1 site.

Figure 8:
FIG. 8 shows an example of a construction map.

Domain 5 of Kininogen 1 1 (D5): D5 was cloned using human genomic DNA isolated from whole blood. The 5' primer introduced an XbaI site. The 5' primer introduced a new NotI site and a novel stop codon to terminate translation. The 382 bp product was amplified by PCR and cloned into pZero-1 (Invitrogen). D5 was then digested out of pZero-1 using XbaI and NotI and ligated into the pLVX-.TRPv1 construct multiple cloning site using xba1 and NotI upstream of the internal ribosomal entry site (IRES) and mCherry. The final construct yielded mouse TRPv1-D5 fusion gene in the pLVX expression vector (FIG. 8a) DNA sequencing confirmed that Domain 5 was in reading frame with TRPv1 and that there was a stop codon on the 3' end of Domain 5.

Expression of TRPv1.D5 in HEK cells: HEK cell expression was performed using transient transfection. Briefly, 1 μg of plasmid was mixed with Lipofectamine LTX with PLUS reagent (Life Technologies) following the manufacturer instructions. Expression was confirmed by standard western blot technique. Once expression was confirmed, pLVX.TRPv1.D5 was co-transfected with a plasmid containing GCaMP6 (addgene). GCaMP6 is a genetically encoded Calcium indicator. Its green fluorescence increases in the presence of increasing amounts of intracellular calcium. Green fluorescence was analyzed in HEK cells using MetaFluor Analyst Software (Molecular Devices) following manufacture instructions. Transfected cells were analyzed prior to RF exposure and during 10 minutes of RF exposure, as discussed below.

Example Set 2

In Vitro Data

Visualization of and Immunoprecipitation Shows Modulation of Ferritin Interaction in HEK-293 Cells TRPV1.D5 redistributes endogenous ferritin to membranes. To visualize subcellular distribution of ferritin, we fused human ferritin with mCherry (FTH1-mCherry) at the C-terminal. Expression of FTH1-mCherry in HEK-293 yielded normal cytoplasmic distribution. FIG. 9a shows that cytoplasmic distribution was not altered with cotransfection of a flagged TRPV1 (i.e., labeled with FLAG). In contrast, co-transfection of FTH1-mCherry and flagged TRPV1.D5 redistributed FTH1-mCherry to cell membranes (FIG. 9b).

FIGS. 9c and 9d show the results of electron microscopy experiments which indicated dense membranes in cells expressing TRPV1.D5, consistent with iron localization at the membranes (FIG. 9d, arrowheads).

Figure 9E:
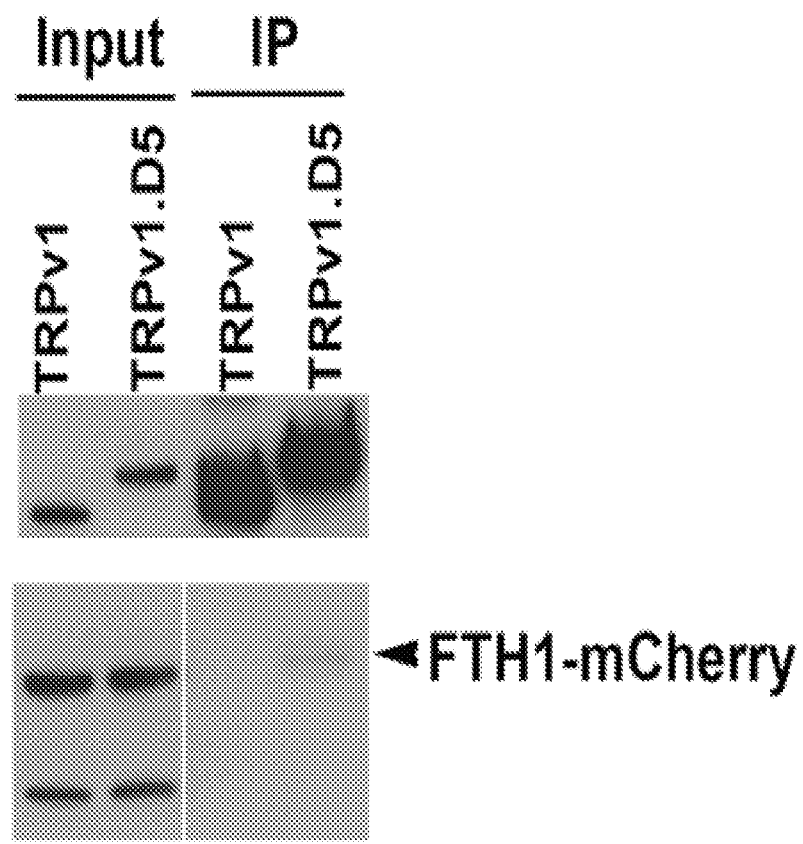
FIG. 9e shows immunoprecipitation experiments; Ferritin-mCherry co-immunoprecipitates with Flag-TRPV1.D5 (i.e., labeled with Flag) but not Flag-TRPV1.

FIG. 9e shows that Ferritin-mCherry co-immunoprecipitated with Flag-TRPV1.D5 but not Flag-TRPV1. Immunoprecipitation of TRPV1.D5 successfully pulled down both ferritin-mCherry and endogenous ferritin (data not shown).

RF Modulation of $Ca^{2+}$ Flow

Figure 10:
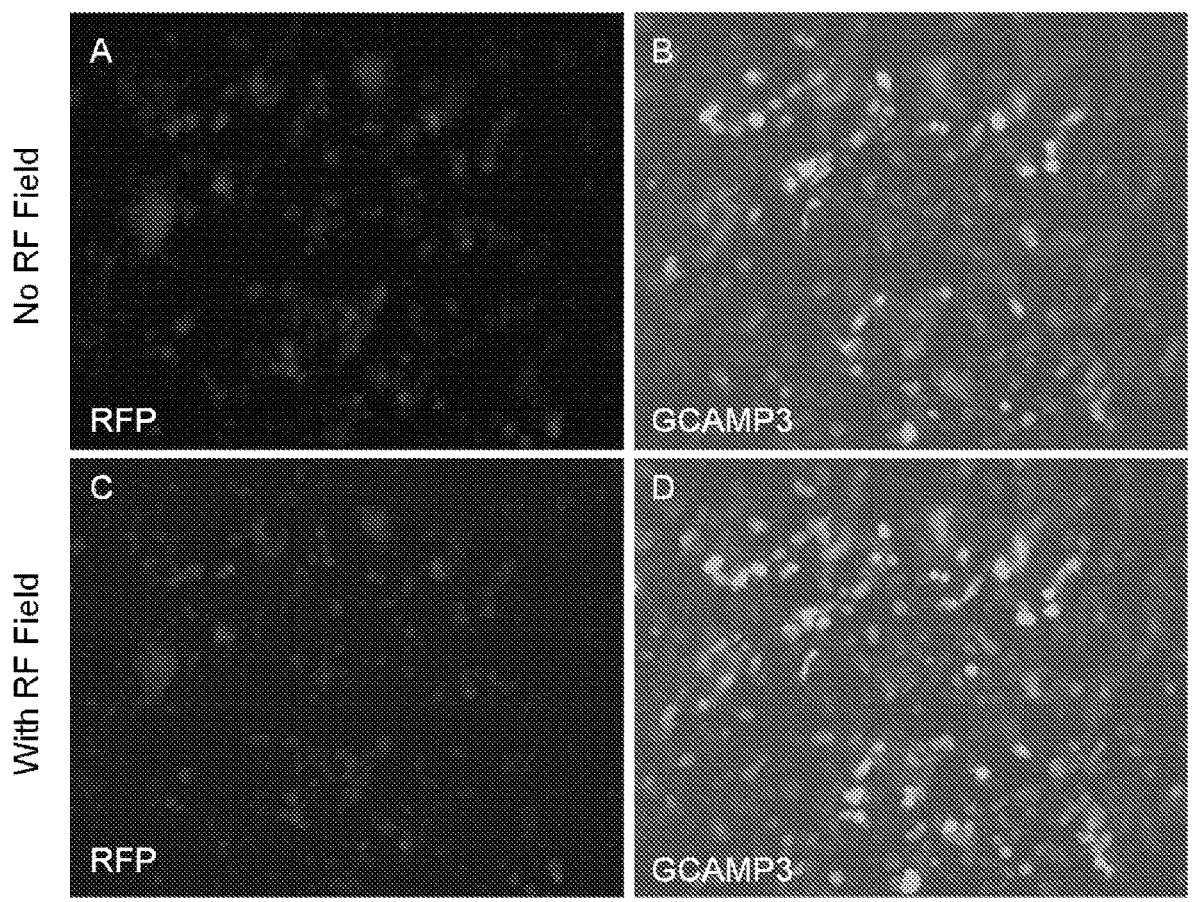
FIG. 10 demonstrates the increased GCAMP3 intensity after the application of EM fields compared to the baseline intensity without EM fields. The red fluorescence indicates the cells that expressed TRPV1.D5.

FIG. 10 demonstrates the increased GCAMP3 intensity after the application of EM fields compared to the baseline intensity without EM fields. The intensity of red fluorescence protein (RFP) indicates the cells that expressed TRPV1.D5 with mCherry. With and without RF fields applied, the intensity of RFP did not change significantly (FIG. 10a and FIG. 10c), demonstrating that the RF fields did not impact mCherry. On the contrary, the intensity of GCAMP3 increased in the presence of RF, indicating an influx of $Ca^{2+}$ to the cells.

Figure 11:
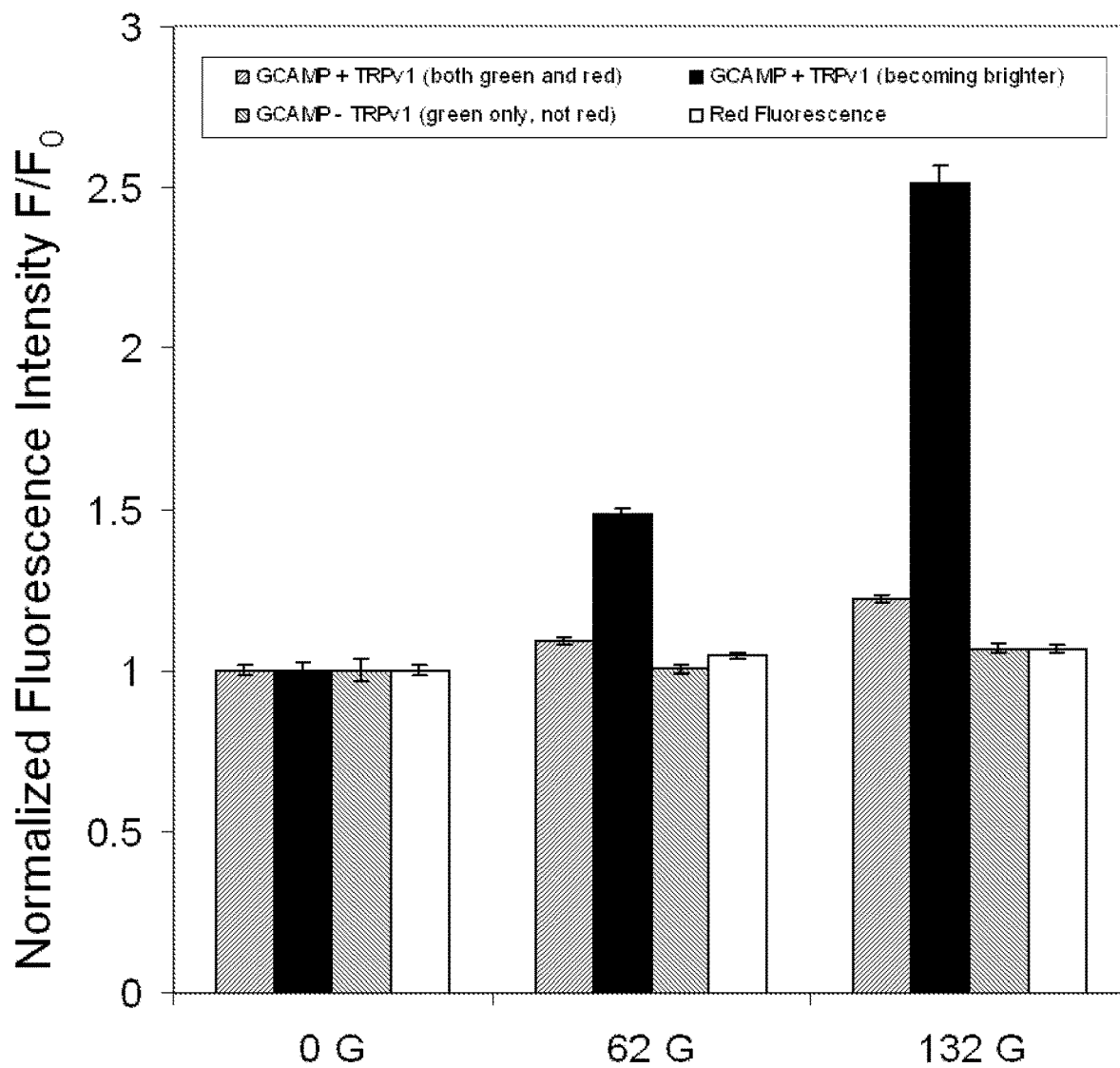
FIG. 11 quantifies the fluorescence intensity at three levels of oscillating electromagnetic fields (RF frequency). Red fluorescence increased by less than 6.5% at the end of experiments. Green fluorescence without TRPV1 increased by less than 6.9%. Green fluorescence of all cells with TRPV1 increased by 9.0% at low magnetic field (62 G) and 22.2% at high magnetic field (132 G). Green fluorescence with TRPV1 that visually became brighter increased by 48.3% at low magnetic field and 151.3% at high magnetic field RF.

FIG. 11 quantifies the fluorescence intensity at three levels of applied electromagnetic fields. Red fluorescence emitted by mCherry ("Red Fluorescence") increased by less than 6.5% at the end of experiments. Green fluorescence (GCaMP3) emitted by GCAMP in cells without TRPV1.D5 ("GCAMP-TRPV1 (green only, not red)") increased by less than 6.9%. Green fluorescence emitted by GCAMP in all cells with TRPV1.D5 ("GCAMP+TRPV1 (both green and red)") increased by 9.0% at low RF (62 G) and 22.2% at high RF (132 G). Green fluorescence emitted by GCAMP in the presence of TRPV1.D5 in cells that visually became brighter ("GCAMP+TRPV1 (becoming brighter)") increased by 48.3% at low RF and 151.3% at high RF. These results showed that GCAMP signal was directly correlated with the RF intensity and the increased GCAMP signal was not due to random ambient fluorescence increase as indicated by the stable red fluorescence.

Figure 12:
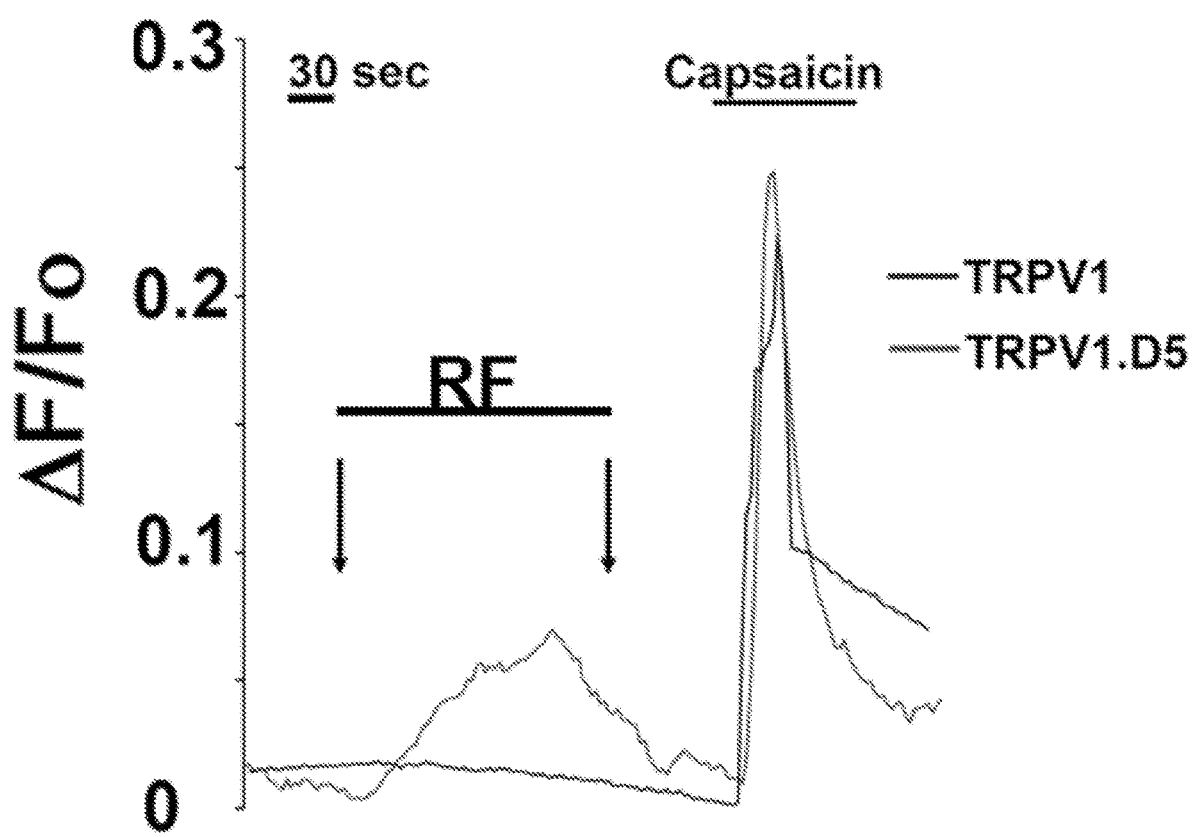
FIG. 12 shows that application of RF to HEK cells with TRPV1.D5 increases $Ca^{2+}$ ion modulation.

A Helmholtz coil (190 MHz) was placed over a petri dish loaded with HEK-293 cells. RF power was supplied by a broadband (0-400 MHz) signal generator and amplified using a 10-W linear amplifier. We used GCaMP as an intracellular calcium indicator whose intensity is proportional to the amount of bound calcium. Using widefield fluorescent microscopy, we measured the change in GCaMP fluorescence in mCherry+ cells expressing TRPV1 and TRPV1.D5 in response to RF stimulation. While both TRPV1 and TRPV1.D5 responded equally well to 1 μM capsaicin, only TRPV1.D5 induced a transient increase in $Ca^{2+}$ permeability following RF (FIG. 12).

Figure 13:
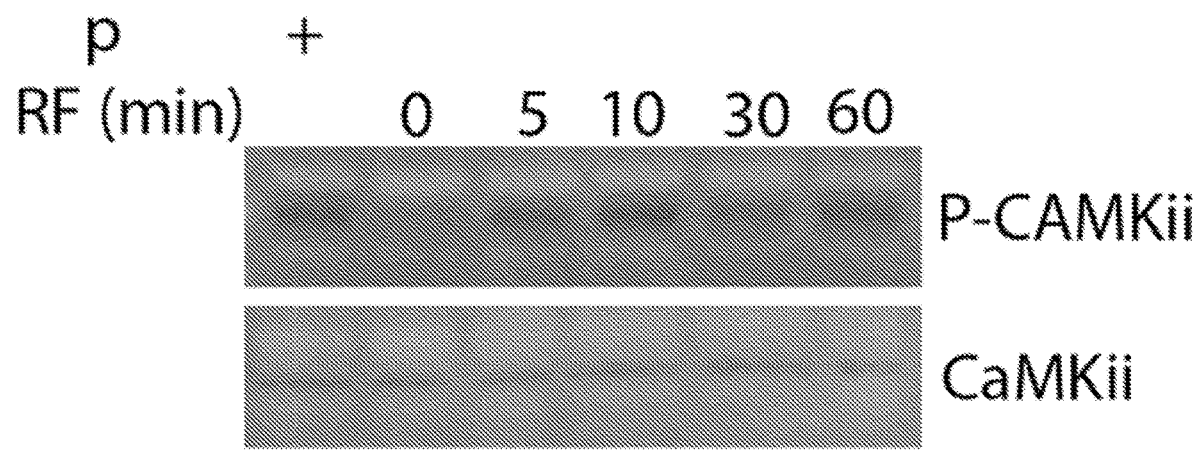
FIG. 13 shows that application of RF to HEK cells with TRPV1.D5 induces p-CaMKii.

FIG. 13 demonstrates an increase in calcium-dependent phosphorylation of CaMKii in TRPv1.D5+ HEK cells following RF stimulation. HEK cells were transiently transfected with TRPv1.D5. 36 hrs after transfection, TRPv1.D5 cells were exposed to RF. At time points indicated, cells were lysed and protein analyzed by western blot for phosphorylation of CaMKii on threonine$^{286}$ (p-CaMKii) using phospho-specific antibodies (top panel). Control cells (0 min) had very little detectable p-CaMKii. As expected, 1 μm Capsaicin (Cap+) induced phosphorylation of CaMKii. The level of p-CaMKii increases in TRPv1.D5+ cells following RF stimulation and peak levels were observed at 10 minutes. Blotting samples for total CaMKii (phosphorylated and nonphosphorylated) reveals similar levels at all time points (bottom panel) indicating that the changes were due to phosphorylation of the target protein.

Example Set 3

In Vivo Data

Modulation of $Ca^{2+}$ Flow In Vivo Produced Congenital Heart Defects

To determine if $Ca^{2+}$ flow could be modulated in vivo, we targeted wild-type TRPV1 or TRPV1.D5 expression to pre-migratory Neural Crest Cells (NCCs) in chicken embryos. NCC migration is dependent on control of $Ca^{2+}$ influx. (See, Hutson et al. 2003) NCCs transverse long distances through the embryo to enable proper heart development (e.g. outflow tracts). We utilized RF to increase $Ca^{2+}$ flow in NCCs while these cells were migrating out of the dorsal neural tube.

Figure 14:
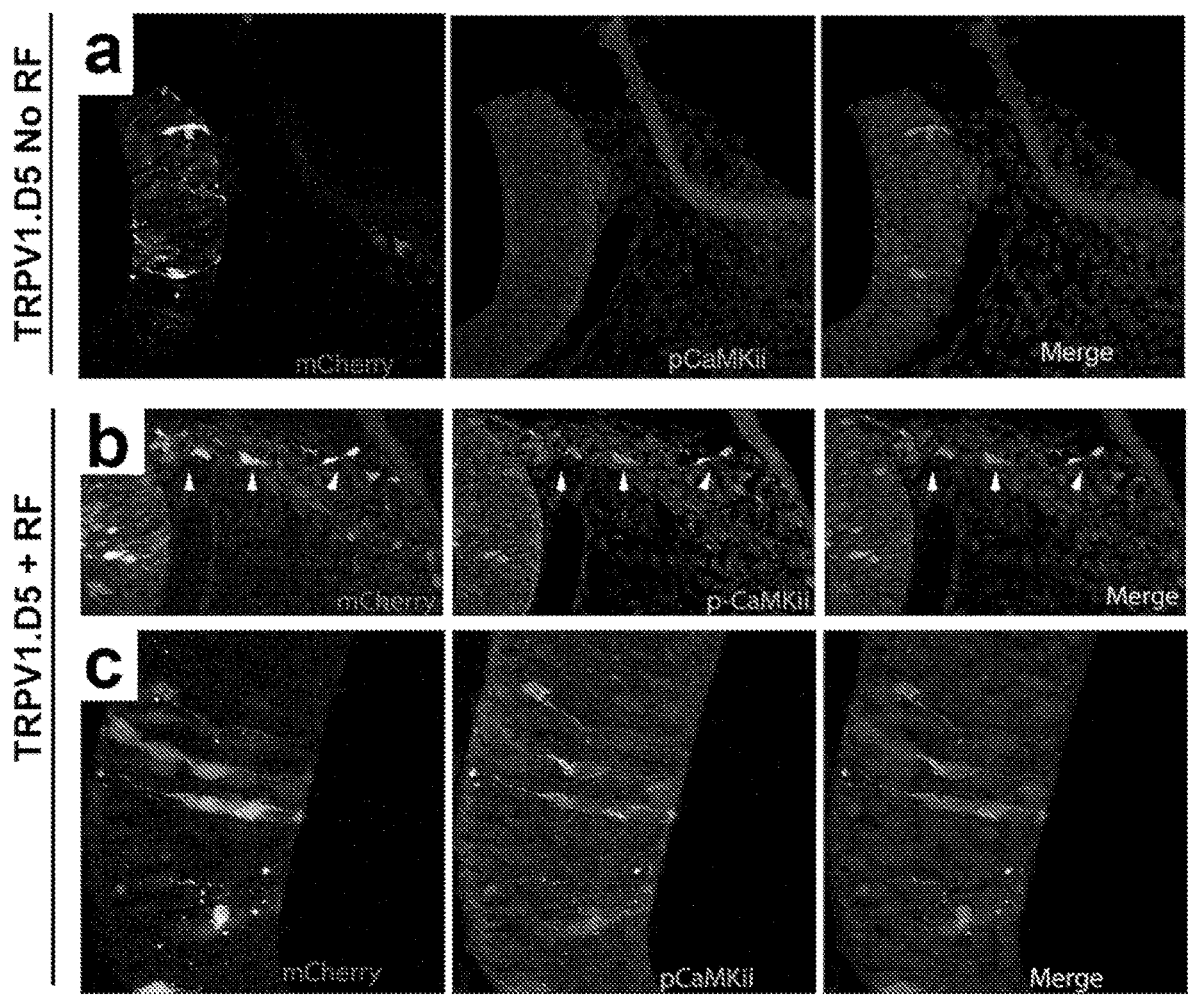
FIG. 14 shows that RF induces phosphorylation of CaMKii in neural crest cells in vivo.

TRPV1.D5 was cloned into pLVX-EF1α-IRES-mCherry vectors. Plasmid DNA was then electroporated in ovo into the dorsal neural tube of chick embryos at Hamburger-Hamilton stage 9-11 to target premigratory NCCs. Twenty four hours later, expression of mCherry was confirmed and eggs were then subjected to no RF (FIG. 14a, control) or 10 minutes of RF (FIG. 14b and FIG. 14c). Immediately afterwards, embryos were removed and fixed in paraformaldehyde. These embryos were cryosectioned and stained for mCherry to identify TRPv1.D5+ cells and phosphorylated CaMKii (p-CaMKii) using an anti-Phospho-CaMKII antibody. In control animals (FIG. 14a) we did not observe detectable levels of p-CaMKii. However, in animals exposed to RF we observed clear co-localization of the mutant channel and p-CaMKii (see right panel in FIG. 14b and FIG. 14c)

Figure 15E:
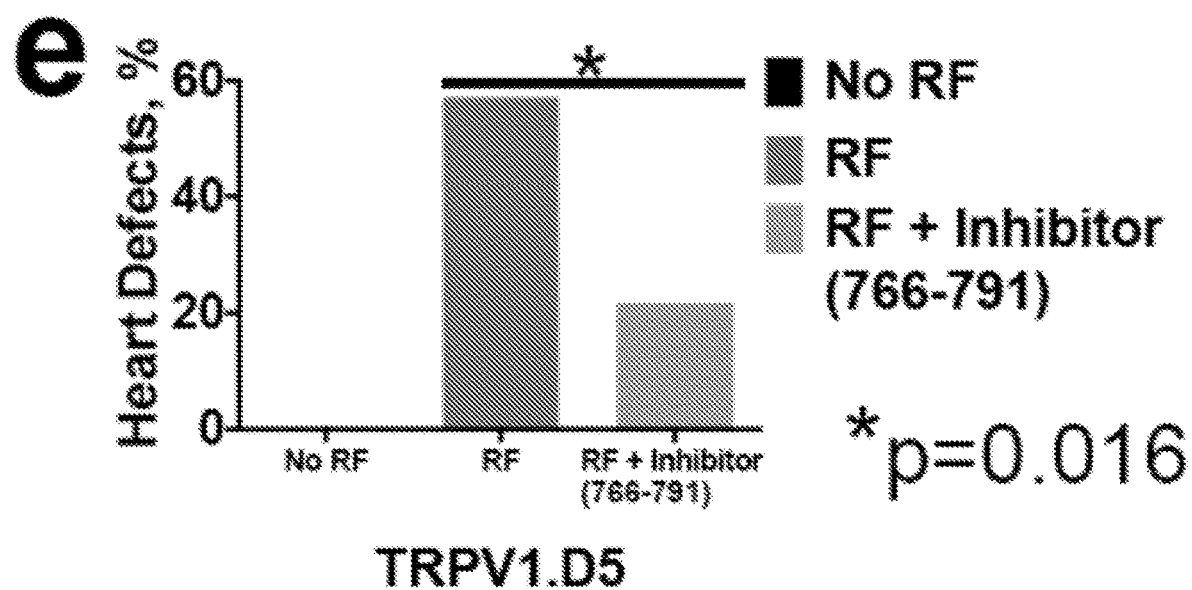
FIG. 15e shows that TRPV1 inhibitor rescues RF induced defects.

At day 10 post experiments, ~60% of the RF-treated TRPV1.D5+ embryos developed congenital heart defects such as ventricular septal defect (VSD), double outlet right ventricle and transposition of great vessels (FIG. 15). Neither the TRPV1 embryos (with or without RF) nor the non-RF treated TRPV1.D5 embryos developed any defects. Further, the defects caused by TRPV1.D5+RF were replicated using wild-type human TRPV1 in chick embryos exposed to capsaicin, supporting that the defects were a result of RF triggered $Ca^{2+}$ activity (data not shown). Additionally, the effect of RF on TRPV1.D5 was reduced by over 65% by TRPV1 antagonist (FIG. 15e). These data demonstrate that $Ca^{2+}$ flow can be modulated in vivo and have the desired effect in the targeted cells.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Ranges indicated with a dash (XX-YY %) are to be interpreted as inclusive of the end points (i.e., XX and YY) of the range. For example, 5-10% should be interpreted as from 5% to 10%, indicating inclusion of the endpoints, 5% and 10%, in the range. As another example, about 5-10% should be interpreted as from about 5% to about 10%, such that the term "about" modifies both end points, here 5% and 10%.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Detailed descriptions of one or more aspects, instances, or embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and any accompanying figures. Such modifications are intended to fall within the scope of the claims.

A number of embodiments have been described. Nevertheless it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments or "other" embodiments may include all or part of "some," "other," and "further" embodiments within the scope of this invention.

What is claimed is:

1. A polypeptide comprising (a) a thermal sensitive ion channel or a variant thereof linked to (b) a domain 5 of kininogen 1 or a variant thereof, wherein the polypeptide has at least 89% sequence identity to SEQ ID NO: 2, at least 89% sequence identity to SEQ ID NO: 4, or at least 89% sequence identity to SEQ ID NO: 6.

2. The polypeptide of claim 1, wherein the polypeptide has at least 90% sequence identity to SEQ ID NO: 2, at least 90% sequence identity to SEQ ID NO: 4, or at least 90% sequence identity to SEQ ID NO: 6.

3. The polypeptide of claim 1, wherein the variant of the thermal sensitive ion channel has at least 90% sequence identity to SEQ ID NO: 8, at least 90% sequence identity to SEQ ID NO: 10, or at least 90% sequence identity to SEQ ID NO: 12.

4. The polypeptide of claim 1, wherein the thermal sensitive ion channel is SEQ ID NO: 8, SEQ ID NO: 10, or SEQ ID NO: 12.

5. The polypeptide of claim 1, wherein the variant of domain 5 of kininogen 1 has at least 90% sequence identity to SEQ ID NO: 14.

6. The polypeptide of claim 1, wherein (a) the thermal sensitive ion channel is SEQ ID NO: 8, SEQ ID NO: 10, or SEQ ID NO: 12, and the variant of the thermal sensitive ion channel has at least 90% sequence identity to SEQ ID NO:

8, at least 90% sequence identity to SEQ ID NO: 10, or at least 90% sequence identity to SEQ ID NO: 12 and (b) the domain 5 of kininogen 1 is SEQ ID NO: 14 and the variant of the domain 5 of kininogen 1 has at least 90% sequence identity to SEQ ID NO: 14.

7. The polypeptide of claim 1, wherein the polypeptide has at least 95% sequence identity to SEQ ID NO: 2, at least 95% sequence identity to SEQ ID NO: 4, or at least 95% sequence identity to SEQ ID NO: 6.

8. The polypeptide of claim 1, wherein the domain 5 of kininogen 1 is SEQ ID NO: 14.

9. The polypeptide of claim 1, wherein the polypeptide is SEQ ID NO: 2, SEQ ID NO:4, or SEQ ID NO:6.

10. A nucleic acid molecule encoding the polypeptide of claim 1.

11. The nucleic acid molecule of claim 10, which comprises a nucleic acid sequence that has at least 90% sequence identity to SEQ ID NO: 1, SEQ ID NO: 3, or SEQ ID NO: 5.

12. The nucleic acid molecule of claim 10, which comprises SEQ ID NO: 1, SEQ ID NO: 3, or SEQ ID NO: 5.

13. A composition comprising the polypeptide of claim 1 or a composition comprising a nucleic acid molecule encoding the polypeptide of claim 1.

14. The composition of claim 13, wherein the amount of the polypeptide or the amount of the nucleic acid is from about 0.0001% (by weight total composition) to about 99%.

15. The composition of claim 13, further comprising an adjuvant, liposome, or carrier.

16. A pharmaceutical composition comprising the polypeptide of claim 1 or a pharmaceutical composition comprising a nucleic acid molecule encoding the polypeptide of claim 1.

17. The pharmaceutical composition of claim 16, wherein the amount of the polypeptide or the amount of the nucleic acid is from about 0.0001% (by weight total composition) to about 50%.

18. The pharmaceutical composition of claim 16, further comprising an adjuvant, liposome, or carrier.

* * * * *